US011669948B2

(12) United States Patent
Tsutsumi et al.

(10) Patent No.: US 11,669,948 B2
(45) Date of Patent: Jun. 6, 2023

(54) LEARNED MODEL GENERATING METHOD, LEARNED MODEL GENERATING DEVICE, PRODUCT IDENTIFYING METHOD, PRODUCT IDENTIFYING DEVICE, PRODUCT IDENTIFYING SYSTEM, AND MEASURING DEVICE

(71) Applicant: Ishida Co., Ltd., Kyoto (JP)

(72) Inventors: Hironori Tsutsumi, Ritto (JP); Kosuke Fuchuya, Ritto (JP)

(73) Assignee: Ishida Co., Ltd., Kyoto (JP)

( * ) Notice: Subject to any disclaimer, the term of this patent is extended or adjusted under 35 U.S.C. 154(b) by 204 days.

(21) Appl. No.: 16/824,573

(22) Filed: Mar. 19, 2020

(65) Prior Publication Data

US 2020/0311903 A1 Oct. 1, 2020

(30) Foreign Application Priority Data

Mar. 28, 2019 (JP) .............................. JP2019-062949

(51) Int. Cl.
*G06N 3/08* (2006.01)
*G06V 10/44* (2022.01)
(Continued)

(52) U.S. Cl.
CPC ............. *G06T 7/0002* (2013.01); *G06N 3/08* (2013.01); *G06N 20/00* (2019.01); *G06V 10/44* (2022.01);
(Continued)

(58) Field of Classification Search
CPC combination set(s) only.
See application file for complete search history.

(56) References Cited

U.S. PATENT DOCUMENTS

2013/0027424 A1 1/2013 Mochizuki et al.
2016/0026900 A1* 1/2016 Ando .................. G06V 10/776
382/159
(Continued)

FOREIGN PATENT DOCUMENTS

CN 108303170 A 7/2018
JP H09-042939 A 2/1997
(Continued)

OTHER PUBLICATIONS

Marc Bosch,"Combining Global and Local Features for Food Identification in Dietary Assessment," Dec. 29, 2011, 2011 18th IEEE International Conference on Image Processing, pp. 1789-1791.*

(Continued)

*Primary Examiner* — Omar S Ismail
(74) *Attorney, Agent, or Firm* — Studebaker & Brackett PC

(57) ABSTRACT

A measuring system 1 includes a server 200 identifying a kind of a product from a product image in which the product is included and a measuring device 100 identifying the kind of the product from the target image in which the product is included. The server 200 includes an acquisition unit that acquires a product image and product information relating to a kind of a product, a dividing unit that acquires a plurality of divided imaged by dividing the product image into a plurality of areas, and a generation unit that generates an identifying model by performing machine learning on the basis of a plurality of divided images extracted by an extraction unit that extracts a plurality of divided images satisfying a predetermined condition relating to a shown amount of the product from among the plurality of divided images.

22 Claims, 15 Drawing Sheets

(51) Int. Cl.
*G06V 20/68* (2022.01)
*G06T 7/00* (2017.01)
*G06N 20/00* (2019.01)

(52) U.S. Cl.
CPC .... *G06T 2207/20081* (2013.01); *G06V 20/68* (2022.01)

(56) References Cited

U.S. PATENT DOCUMENTS

| | | | |
|---|---|---|---|
| 2017/0206646 A1* | 7/2017 | Jung | G06F 16/51 |
| 2018/0075315 A1* | 3/2018 | Gu | G06T 7/0002 |
| 2019/0095300 A1* | 3/2019 | Oba | G06N 20/00 |
| 2019/0147582 A1* | 5/2019 | Lee | G06T 11/00 382/156 |
| 2020/0005492 A1* | 1/2020 | Higa | G06T 7/11 |
| 2020/0013169 A1* | 1/2020 | Higa | G06V 10/764 |
| 2020/0311903 A1* | 10/2020 | Tsutsumi | G06V 10/44 |

FOREIGN PATENT DOCUMENTS

| | | |
|---|---|---|
| JP | 2013-117861 A | 6/2013 |
| JP | 2015-064628 A | 4/2015 |
| JP | 2017-117019 A | 6/2017 |
| JP | 2017-182653 A | 10/2017 |
| JP | 2018-169752 A | 11/2018 |
| JP | 2017-016268 A | 1/2019 |
| JP | 2002-329188 A | 11/2022 |

OTHER PUBLICATIONS

Ye He,"Context Based Food Image Analysis,"Sep. 26, 2013,2013 IEEE International Conference on Multimedia and Expo (ICME),pp. 2748-2751.*

Ye He,"Food Image Analysis: Segmentation, Identification and Weight Estimation,"Sep. 26, 2013,2013 IEEE International Conference on Multimedia and Expo (ICME), pp. 1-5.*

Fengqing Zhu,"Multiple Hypotheses Image Segmentation and Classification With Application to Dietary Assessment," Feb. 6, 2014,IEEE Journal of Biomedical and Health Informatics, vol. 19, Issue: 1, Jan. 2015,pp. 377-386.*

Yuji Matsuda,"Recognition Of Multiple-Food Images By Detecting Candidate Regions,"Sep. 13, 2012,2012 IEEE International Conference on Multimedia and Expo,pp. 25-29.*

Mohammed Ahmed Subhi,"Vision-Based Approaches for Automatic Food Recognition and Dietary Assessment: A Survey," Mar. 13, 2019,IEEE Access,vol. 7,pp. 35370-35377.*

The extended European search report issued by the European Patent Office dated Jan. 14, 2021 which corresponds to European Patent Application No. 20165466.2-1207 and is related to U.S. Appl. No. 16/824,573.

He Ye et al.; "Food Image Analysis: Segmentation Identification and Weight Estimation"; 2013 IEEE Internationl conference on Multimedia and Expo (ICME); Jul. 15, 2013; pp. 1-6; XP032488045; IEEE.

The partial European search report issued by the European Patent Office dated Sep. 9, 2020, which corresponds to European Patent Application No. 20165466.2-1207 and is related to U.S. Appl. No. 16/824,573.

* cited by examiner

LEARNED MODEL GENERATING METHOD, LEARNED MODEL GENERATING DEVICE, PRODUCT IDENTIFYING METHOD, PRODUCT IDENTIFYING DEVICE, PRODUCT IDENTIFYING SYSTEM, AND MEASURING DEVICE

TECHNICAL FIELD

One aspect of the present invention relates to a learned model generating method, a learned model generating device, a product identifying method, a product identifying device, and a measuring device.

BACKGROUND

Conventionally, methods for identifying a product on the basis of an image in which the product is included are known. For example, in a product identifying method described in Patent Document 1 (Japanese Unexamined Patent Publication No. 2015-64628), a feature quantity of an image of a product is extracted, and a kind of the product is identified by comparing the feature quantity with feature quantities included in learning data.

SUMMARY

As products that are sold in supermarkets and the like, for example, there are salads and side dishes. In the salads, the side dishes, and the like, a plurality of foods are mixed, and the shapes thereof are not fixed. In this way, in a case in which a shape of a product is an irregular shape, it is difficult to acquire a feature quantity of the product. For this reason, the accuracy of identification of a product may decrease.

An object of one aspect of the present invention is to provide a learned model generating method, a learned model generating device, a product identifying method, a product identifying device, and a measuring device achieving improvement of accuracy of identification of products.

According to one aspect of the present invention, there is provided a learned model generating method that is a method of generating an identifying model for identifying a kind of a product from a product image in which the product is included, the learned model generating method including: acquiring the product image and product information relating to the kind of the product; acquiring a plurality of divided images by dividing the product image into a plurality of areas; extracting predetermined divided images on the basis of a predetermined condition relating to a shown amount of the product from among the plurality of divided images; and generating the identifying model by performing machine learning by associating the plurality of divided images extracted in the extracting of predetermined divided images with the product information.

In the learned model generating method according to one aspect of the present invention, predetermined divided images are extracted on the basis of a predetermined condition relating to a shown amount of the product from among the plurality of divided images. The divided images include an image in which only a product is shown, an image in which a product and objects other than a product (a container, a background, and the like) are shown, and an image in which only objects other than a product are shown. In the learned model generating method, divided images are extracted from such divided images on the basis of the predetermined condition, and machine learning is performed on the basis of the extracted divided images. In accordance with this, in the learned model generating method, machine learning based on appropriate teach images can be performed. Therefore, according to the learned model generating method, an identifying model having an improved product identifying accuracy can be generated.

In one embodiment, a plurality of divided images satisfying the predetermined condition may be extracted from among the plurality of divided images in the extracting of predetermined divided images. According to this method, machine learning based on appropriate teacher images can be performed. Therefore, according to the learned model generating method, an identifying model having an improved product identifying accuracy can be generated.

In one embodiment, divided images in which a shown amount of objects other than the product is equal to or smaller than a threshold may be extracted in the extracting of predetermined divided images. In other words, divided images in which the shown amount of the product is larger than a threshold are extracted in the extracting of predetermined divided images. In this method, divided images having high product occupancy rates are extracted. In other words, in the learned model generating method, divided images in which a container and a background other than the product are shown can be excluded. For this reason, in the learned model generating method, machine learning can be performed using divided images in which the product is shown. Therefore, in the learned model generating method, an identifying model having an improved product identifying accuracy can be generated.

In one embodiment, a non-product likelihood indicating a likelihood of being the divided image not including the product is acquired for each of the plurality of divided images using an extraction model generated using machine learning based on images in which the product is not included, and divided images of which the non-product likelihoods are equal to or lower than a threshold may be extracted in the extracting of predetermined divided images. In this method, only divided images in which the product is shown can be appropriately extracted.

In one embodiment, the extraction model may be generated by acquiring a non-product image in which the product is not included, acquiring a plurality of non-product divided images by dividing the non-product image into a plurality of areas, and generating the extraction model by performing machine learning on the basis of the plurality of non-product divided images. In accordance with this, in the learned model generating method, an extraction model can be appropriately generated.

In one embodiment, the product image may be divided such that all the areas exhibit rectangular shapes and have the same dimensions for each of the plurality of divided images in the acquiring of a plurality of divided images by performing dividing, and the non-product image may be divided such that the areas have the same shape and the same dimension as those of the divided image for each of the plurality of non-product divided images in the acquiring of a plurality of non-product divided images. In this method, since the divided image and the non-product divided image having the same shapes and the same dimensions, a conversion process for converting the shape and the size of the image does not need to be performed. Therefore, in the learned model generating method, the process load is reduced.

In one embodiment, one divided image in which a shown amount of objects other than the product is equal to or smaller than a threshold and other divided images in which shown amounts of objects other than the product are larger than a threshold are extracted from the plurality of divided images, the product information is associated with the one divided image, and non-product information indicating an object other than the product is associated with the other divided images in the extracting of predetermined divided images, and the identifying model may be generated by performing machine learning based on the one divided image and the other divided images extracted in the extracting of predetermined divided images in the generating of the identifying model. In this method, machine learning is performed on the basis of the divided images with which the product information is labeled and other images with which the non-product information is labeled. In this way, since machine learning is performed by identifying (classifying) divided images in which the product is shown and divided images in which the shown amount of the product is small (not shown), an identifying model having an improved product identifying accuracy can be generated.

In one embodiment, divided images of which pixel inclusion ratios are equal to or lower than a predetermined threshold among a plurality of divided target images may be extracted on the basis of feature quantities of pixels of an image in which the product is not included in the extracting of predetermined divided images in the generating of the identifying model. In this method, only divided images in which the product is shown can be appropriately extracted.

In one embodiment, the product image may be divided such that one divided image and the other divided images overlap each other at least partially in the acquiring of a plurality of divided images by performing dividing. In this method, when a product image is divided, even in a case in which one product included in products is broken in one divided image, there are cases in which the entirety of one product enters another divided image. For this reason, in the measuring learned model generating method, since machine learning based on appropriate teacher images can be performed, an identifying model having an improved product identifying accuracy can be generated.

In one embodiment, the areas acquired by dividing the product image is set such that other areas are moved by a predetermined amount with respect to the one area in a first direction that is an arrangement direction of pixels of the product image or a second direction that is orthogonal to the first direction in the acquiring of a plurality of divided images by performing dividing. In this method, by moving the area by a predetermined amount, the product image can be divided such that each pixel is included in each of areas aligned in the movement direction the same number of times.

In one embodiment, the product image may be divided such that all the areas exhibit rectangular shapes and have the same dimensions for each of the plurality of divided images in the acquiring of a plurality of divided images by performing dividing. In this method, since all the divided images have the same shapes and the same dimensions, a conversion process for converting the shape and the size of the images does not need to be performed. Therefore, according to the learned model generating method, the process load is reduced.

In one embodiment, comparing the product image with a base image not including the product and cutting a product area, in which at least the entire product is included, smaller than the product image from the product image is included, and the plurality of divided images are acquired by dividing the product area into the plurality of areas in the acquiring of a plurality of divided images by performing dividing. In this method, since a product area acquired by excluding parts other than the product from the product image is divided, an unnecessary area does not need to be divided. Therefore, according to the learned model generating method, the process load is reduced.

According to one aspect of the present invention, there is provided a learned model generating device that is a device generating an identifying model for identifying a kind of a product from a product image in which the product is included, the learned model generating device including: an acquisition unit acquiring the product image and product information relating to the kind of the product; a dividing unit acquiring a plurality of divided images by dividing the product image into a plurality of areas; an extraction unit extracting a plurality of divided images on the basis of a predetermined condition relating to a shown amount of the product from among the plurality of divided images; and a generation unit generating the identifying model by performing machine learning on the basis of a plurality of the divided images extracted by the extraction unit.

In the learned model generating device according to one aspect of the present invention, predetermined divided images are extracted on the basis of a predetermined condition relating to a shown amount of the product from among the plurality of divided images. The divided images include an image in which only a product is shown, an image in which a product and objects other than a product (a container, a background, and the like) are shown, and an image in which only objects other than a product are shown. In the learned model generating device, divided images are extracted from such divided images on the basis of the predetermined condition, and machine learning is performed on the basis of the extracted divided images. In accordance with this, in the learned model generating device, machine learning based on appropriate teach images can be performed. Therefore, according to the learned model generating device, an identifying model having an improved product identifying accuracy can be generated.

A product identifying method according to one aspect of the present invention is a product identifying method of identifying a kind of a product from a target image in which the product is included using an identifying model generated using the learned model generating method described above, the product identifying method including: acquiring a plurality of divided target images by dividing the target image into a plurality of areas; acquiring a plurality of divided target images satisfying a predetermined condition relating to a shown amount of the product from among the plurality of divided target images; and acquiring a process result acquired by performing a process using the identifying model for the plurality of divided target images acquired in the acquiring of a plurality of divided target images satisfying a predetermined condition and identifying a kind of the product on the basis of the process result.

In the product identifying method according to one aspect of the present invention, a kind of the product is identified using the identifying model described above. Accordingly, in the product identifying method, a product identifying accuracy is improved. In addition, in this product identifying method, a plurality of divided target images satisfying a predetermined condition relating to a shown amount of the product are extracted from among the plurality of divided target images. The divided target images include an image in which only a product is shown, an image in which a product and objects other than a product (a container, a background, and the like) are shown, and an image in which only objects other than a product are shown. In the product identifying method, divided target images satisfying a predetermined condition are acquired from among such divided target images, and a process using the identifying model is performed for the acquired divided target images. In accordance with this, in the product identifying method, a process based on appropriate divided target images can be performed. Therefore, according to the product identifying method, the product identifying accuracy is improved.

In one embodiment, divided target images in which the shown amount of objects other than the product is equal to or smaller than a threshold may be acquired in the acquiring of a plurality of divided target images satisfying a predetermined condition. In this method, divided images having high product occupancy rates are acquired. In other words, divided images in which a container and a background other than the product are shown can be excluded. For this reason, in the product identifying method, the product identifying accuracy is improved.

In one embodiment, a non-product likelihood indicating a likelihood of being the divided target image not including the product is acquired for each of the plurality of divided target images using an acquisition model generated using machine learning based on an image in which the product is not included, and divided target images of which non-product likelihoods are equal to or smaller than a threshold may be acquired in the acquiring of a plurality of divided target images satisfying a predetermined condition. In this method, only divided target images in which the product is shown can be appropriately acquired.

In one embodiment, the target image may be divided such that the areas exhibit rectangular shapes and have the same dimensions for each of the plurality of divided target images in the acquiring of a plurality of divided target images by dividing the target image. In this method, since all the divided target images have the same shapes and the same dimensions, a conversion process for converting the shape and the size of an image does not need to be performed. Therefore, according to the product identifying method, the process load is reduced.

According to one aspect of the present invention, there is provided a product identifying method of identifying a kind of a product from a target image in which the product is included using an identifying model generated using the learned model generating method described above, the product identifying method including: acquiring a plurality of divided target images by dividing the target image into a plurality of areas; and acquiring a product likelihood indicating a likelihood of being the product and a non-product likelihood indicating a likelihood of being an object other than the product in a process result acquired by performing a process using the identifying model for the plurality of divided target images acquired in the acquiring of a plurality of divided target images and identifying a kind of the product on the basis of the product likelihood.

In the product identifying method according to one aspect of the present invention, a kind of the product is identified using the identifying model described above. Accordingly, in the product identifying method, a product identifying accuracy is improved. In addition, in the product identifying method, a product likelihood indicating a likelihood of being the product and a non-product likelihood indicating a likelihood of being an object other than the product are acquired in a process result acquired by performing a process using the identifying model, and a kind of the product is identified on the basis of the product likelihood. In accordance with this, in the product identifying method, the product identifying accuracy is improved.

In one embodiment, a plurality of process results are acquired by performing the process using the identifying model for each of the plurality of divided target images, and the kind of the product may be identified on the basis of the plurality of process results in the acquiring of a product likelihood and a non-product likelihood and the identifying of a kind of the product. In this method, since a plurality of process results are acquired by performing the process using the identifying model for individual divided target images, the product identifying accuracy can be further improved.

In one embodiment, weighting is performed for the process result on the basis of a magnitude of a degree of a product likelihood indicating a likelihood of the product being one kind, and the kind of the product may be identified on the basis of a majority decision of weightings assigned to the process result in the acquiring of a product likelihood and a non-product likelihood and the identifying of a kind of the product. According to this method, the product can be identified with a higher accuracy.

In one embodiment, in a case in which a plurality of products are included in the target image, a kind of each of the plurality of products may be identified on the basis of the process result for each area including each of the plurality of products in the acquiring of a product likelihood and a non-product likelihood and the identifying of a kind of the product. In this method, a kind can be identified for each of a plurality of products included the target image.

According to one aspect of the present invention, there is provided a product identifying device that identifies a kind of a product from a target image in which the product is included using an identifying model generated using the learned model generating method described above, the product identifying device including: a first acquisition unit acquiring a plurality of divided target images by dividing the target image into a plurality of areas; a second acquisition unit acquiring a plurality of divided target images satisfying a predetermined condition relating to a shown amount of the product from among the plurality of divided target images; and an identifying unit acquiring a process result acquired by performing a process using the identifying model for the plurality of divided target images acquired by the second acquisition unit and identifying the kind of the product on the basis of the process result.

In the product identifying device according to one aspect of the present invention, a kind of the product is identified using the identifying model described above. Accordingly, in the product identifying device, a product identifying accuracy is improved. In addition, in this product identifying device, a plurality of predetermined divided target images satisfying a predetermined condition relating to a shown amount of the product are extracted from among the plurality of divided target images. The divided target images include an image in which only a product is shown, an image in which a product and objects other than a product (a container, a background, and the like) are shown, and an image in which only objects other than a product are shown. In the product identifying device, divided target images satisfying a predetermined condition are acquired from among such divided target images, and a process using the identifying model is performed for the acquired divided target images. In accordance with this, in the product identifying device, a process based on appropriate divided target images can be performed. Therefore, according to the product identifying device, the product identifying accuracy is improved.

A product identifying system according to one aspect of the present invention is a product identifying system including: a generation device generating an identifying model used for identifying a kind of a product from a product image in which the product is included; and an identifying device identifying the kind of the product from a target image in which the product is included, the generation device includes: an acquisition unit acquiring the product image and product information relating to the kind of the product; a dividing unit acquiring a plurality of first divided images by dividing the product image into a plurality of areas; an extraction unit extracting a plurality of first divided images satisfying a predetermined condition relating to a shown amount of the product from among the plurality of first divided images; and a generation unit generating the identifying model by performing machine learning by associating the plurality of first divided images extracted by the extraction unit with the product information, and the identifying device includes: a first acquisition unit acquiring a plurality of second divided images by dividing the target image into a plurality of areas; a second acquisition unit acquiring a plurality of second divided images satisfying a predetermined condition relating to a shown amount of the product from among the plurality of second divided images; and an identifying unit acquiring a process result acquired by performing a process using the identifying model for the plurality of second divided images acquired by the second acquisition unit and identifying the kind of the product on the basis of the process result.

In addition, in the generation device of the product identifying system according to one aspect of the present invention, a plurality of first divided images satisfying a predetermined condition relating to a shown amount of the product are extracted from among the plurality of divided images. The first divided images include an image in which only a product is shown, an image in which a product and objects other than a product (a container, a background, and the like) are shown, and an image in which only objects other than a product are shown. In the generation device, first divided images satisfying a predetermined condition are extracted from among such first divided images, and machine learning is performed on the basis of the extracted first divided images. In accordance with this, in the generation device, machine learning based on appropriate teach images can be performed. Therefore, according to the generation device, an identifying model having an improved product identifying accuracy can be generated.

In addition, in the identifying device of the product identifying system, a plurality of divided images satisfying a predetermined condition relating to the shown amount of the product are extracted from among the plurality of second divided images. The identifying device acquires second divided images satisfying a predetermined condition from among the second divided images and performs a process using the identifying model for the acquired second divided images. In accordance with this, the identifying device can perform a process based on appropriate second divided images. Therefore, the product identifying system can improve the product identifying accuracy.

A measuring device according to one aspect of the present invention is a measuring device that identifies a kind of a product from a target image in which the product is included using an identifying model generated using the learned model generating method described above and calculates a price of the product, the measuring device including: a measuring unit measuring a weight of the product; an imaging unit imaging the product; an identifying unit acquiring a process result acquired by performing a process using the identifying model for the target image that is imaged by the imaging unit and identifying the kind of the product on the basis of the process result; and a calculation unit calculating a price of the product on the basis of the weight of the product measured by the measuring unit and the kind of the product identified by the identifying unit.

The measuring device according to one aspect of the present invention identifies a kind of the product using the identifying model described above. Therefore, according to the measuring device, the product identifying accuracy is improved.

According to one aspect of the present invention, the product identifying accuracy can be improved.

DETAILED DESCRIPTION

Hereinafter, a preferred embodiment of the present invention will be described in detail with reference to the attached drawings. In description of the drawings, the same reference signs will be assigned to the same or corresponding elements, and duplicate description thereof will be omitted.

Figure 1:
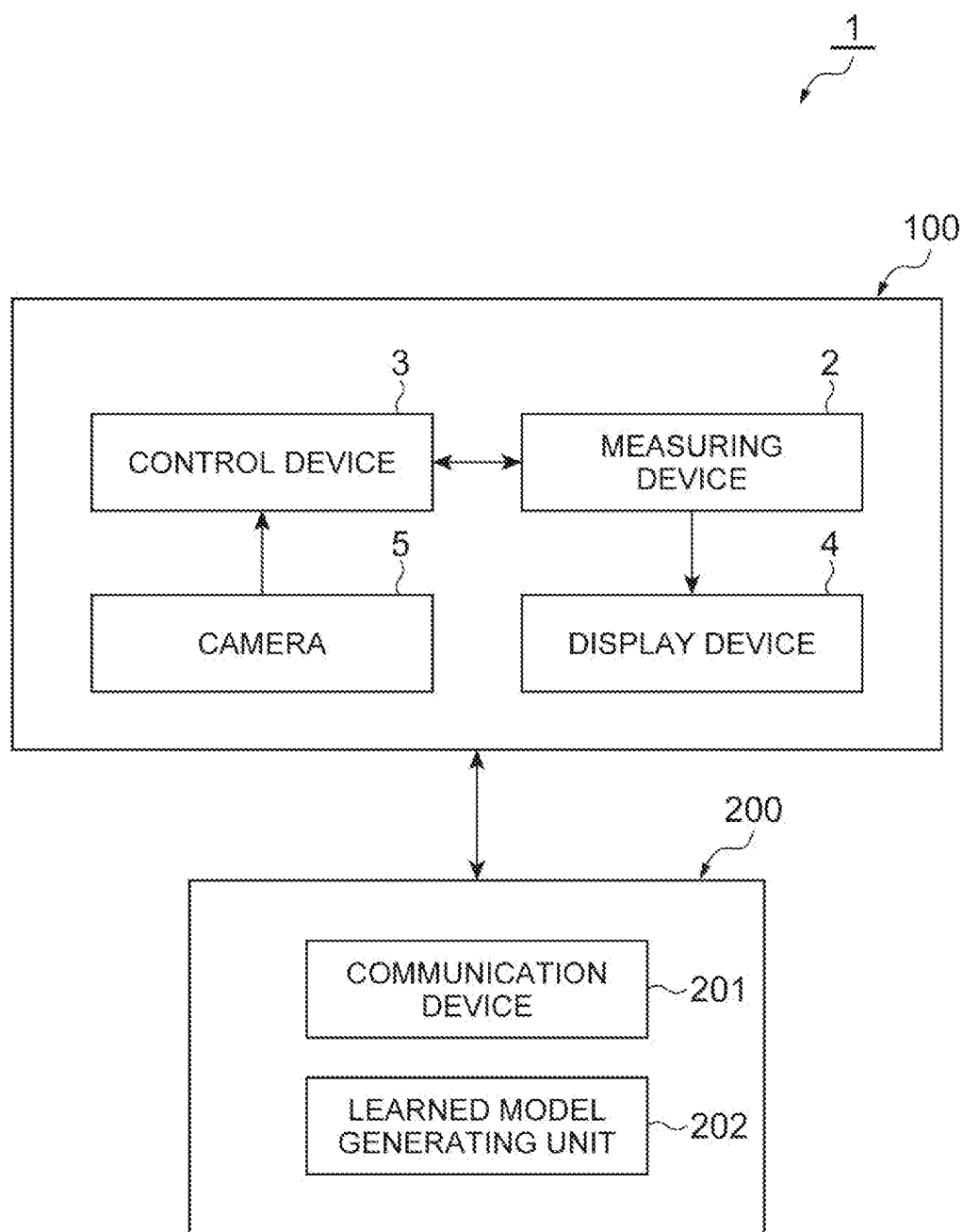
FIG. 1 is a diagram illustrating the configuration of a measuring device according to one embodiment.

As illustrated in FIG. 1, a measuring system (a product identifying system) 1 includes a measuring device (a product identifying device) 100 and a server (a learned model generating device) 200. The measuring device 100 and the server 200 are communicatively connected.

The measuring device 100 includes a measuring device 2, a control device 3, a display device 4, and a camera (an imaging unit) 5. The measuring device 2 and the control device 3 are communicatively connected. The control device 3 and the camera 5 are communicatively connected. The measuring device 2 and the display device 4 are communicatively connected.

The measuring device 2 is an electronic scale. The measuring device 2 has a function of measuring a weight of a product S (see FIG. 6) and issuing a label LC to be attached to a measured product S. In this embodiment, the product S is a food (a salad, a daily dish) or the like put into a container P. Here, the container P includes a transparent lid part. The lid part is colored or colorless and is formed using a material that transmits light. The camera 5 images products S inside the container P by imaging light that is transmitted through the lid part of the container P.

Figure 2:
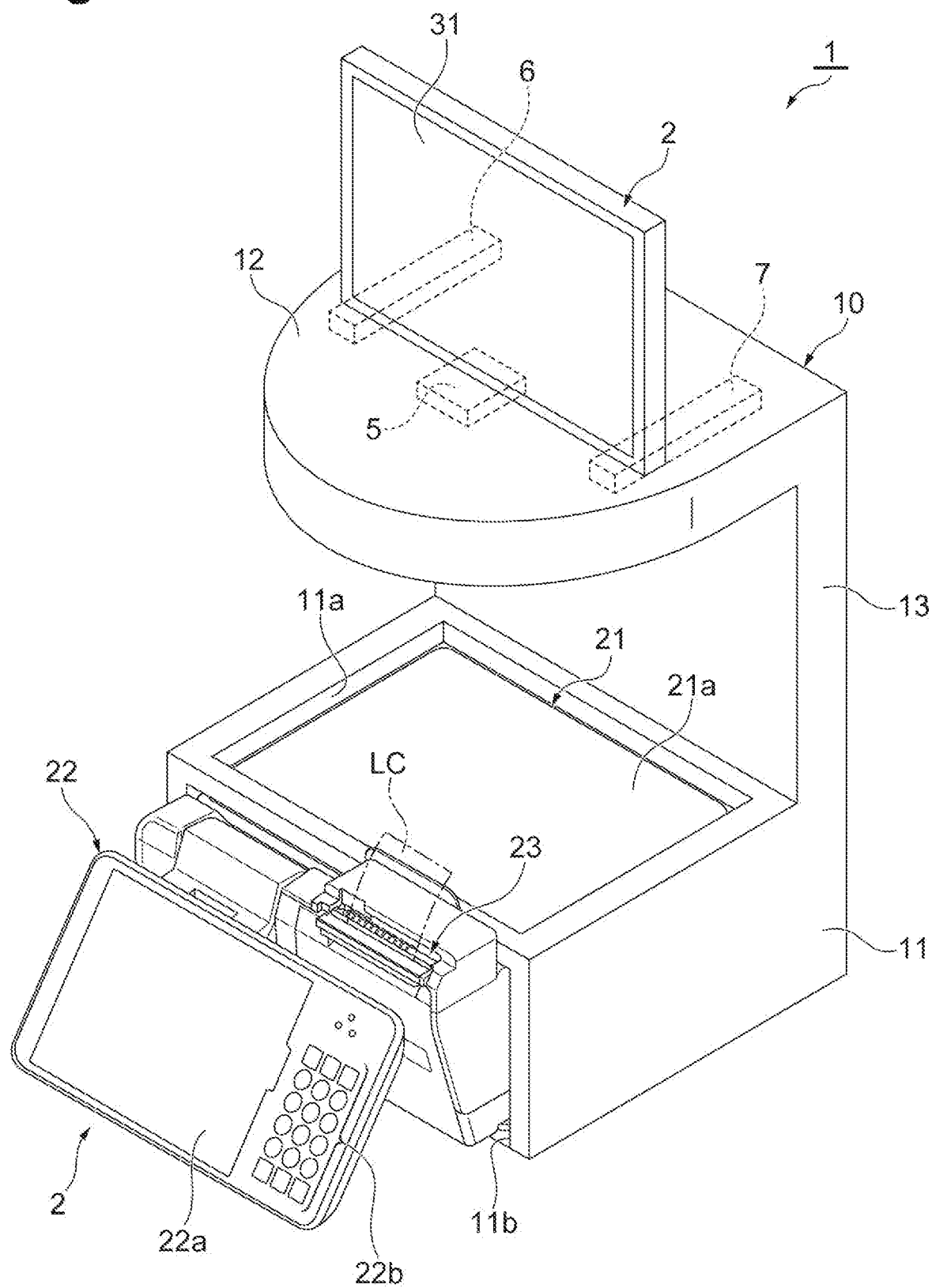
FIG. 2 is a perspective view illustrating a measuring device.

As illustrated in FIG. 2, in this embodiment, the measuring device 2 is accommodated in a casing 10. The casing 10 includes an accommodation part 11, a holding part 12, and a connection part 13. The accommodation part 11 accommodates the measuring device 2. The accommodation part 11 has a box shape. In the accommodation part 11, a first opening part 11a that exposes a measurement stand 21a of a measuring unit 21 of the measuring device 2 and a second opening part 11b that exposes an operation unit 22 of the measuring device 2 are formed.

The control device 3, the camera 5, a first lighting unit 6, and a second lighting unit 7 are disposed in the holding part 12. The holding part 12 is disposed on the accommodation part 11. The control device 3 is disposed on the holding part 12. The connection part 13 connects the accommodation part 11 and the holding part 12. The connection part 13 extends in a vertical direction. The display device 4 is disposed on a rear face of the connection part 13. The display device 4, for example, is a liquid crystal display. The display device 4 performs display for a customer.

The camera 5 is disposed at a position facing the measurement stand 21a (to be described below) above the measurement stand 21a of the measuring device 2. The camera 5 outputs captured image data to the control device 3. In addition, the camera 5 outputs the captured image data to the server 200.

For example, the first lighting unit 6 and the second lighting unit 7 are LED lamps. The first lighting unit 6 and the second lighting unit 7 are disposed at positions facing the measurement stand 21a above the measurement stand 21a of the measuring device 2. The first lighting unit 6 and the second lighting unit 7 are arranged with a predetermined gap interposed therebetween in a widthwise direction of the casing 10. More specifically, the first lighting unit 6 and the second lighting unit 7 are arranged at positions having the camera 5 interposed therebetween in the widthwise direction of the casing 10.

Figure 3:
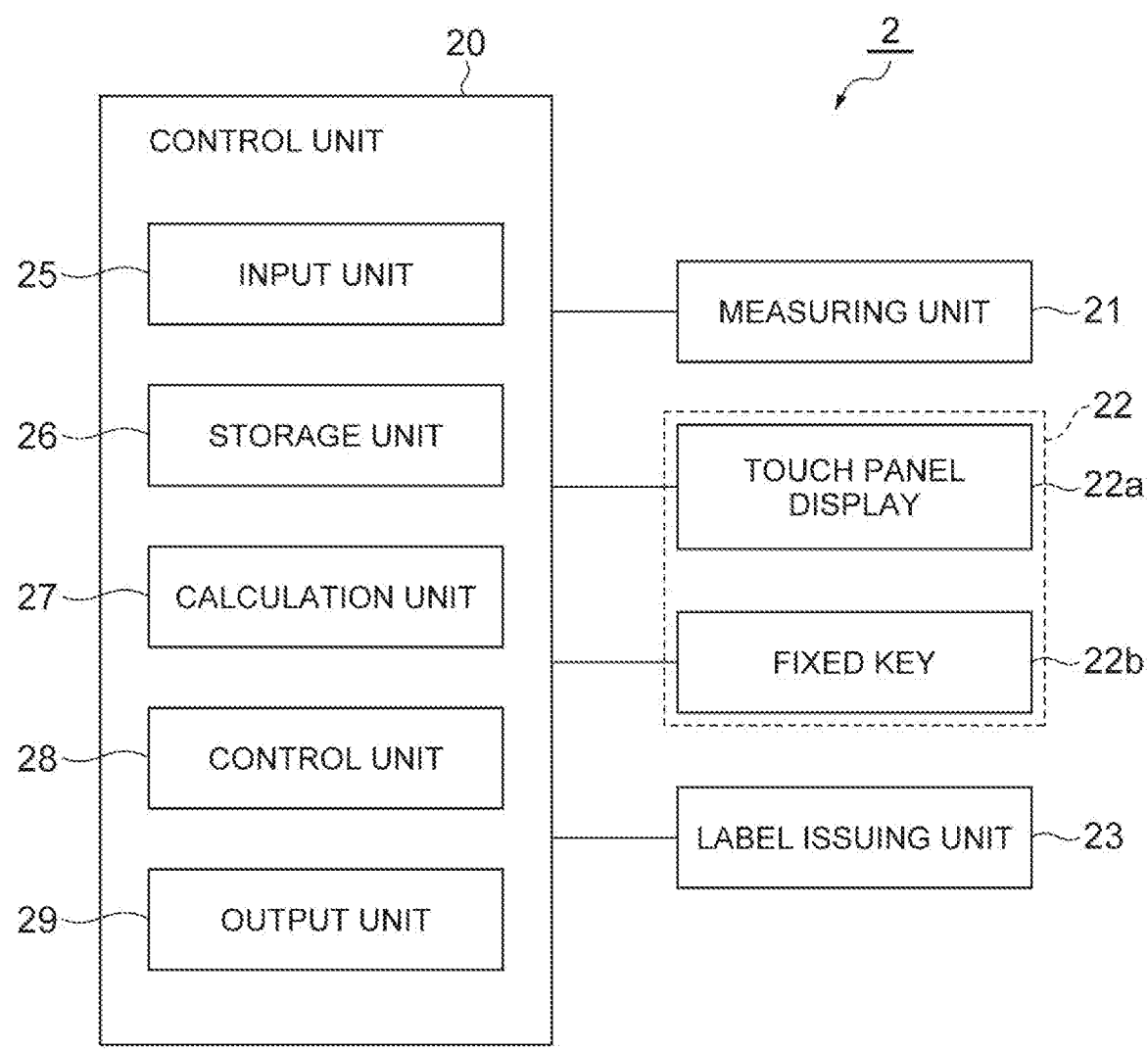
FIG. 3 is a diagram illustrating the configuration of a measuring device.

As illustrated in FIG. 3, the measuring device 2 includes a control unit 20, a measuring unit 21, an operation unit 22, and a label issuing unit 23.

The control unit 20 is a part that controls various operations of the measuring device 2 and is configured to include a central processing unit (CPU), a read only memory (ROM), a random access memory (RAM), and the like. The control unit 20 controls display of a touch panel display 22a to be described below.

The measuring unit 21 is configured to include the measurement stand 21a, a load cell not illustrated in the drawing, a signal processing circuit, and a transmission module. A product S is placed on the measurement stand 21a. The load cell is disposed below the measurement stand 21a. The load cell converts a mechanical distortion occurring in accordance with a measuring object placed on the measurement stand 21a into an electric signal. The signal processing circuit amplifies an electric signal output form the load cell and converts the electric signal into a digital signal. The transmission module outputs the digital signal to the control unit 20.

The operation unit 22 includes a touch panel display 22a and a fixed key 22b. On the touch panel display 22a, information relating to a product S measured by the measuring device 2, basic information required for an operation of the measuring device 2, and the like are displayed in accordance with control of the control unit 20. In the fixed key 22b, there are a "unit price" key, a "fixed amount" key, a "tare" key, a "print" key, a "call" key, and the like that are necessary as charge scales, and these are appropriately disposed together with numeric keys.

The label issuing unit 23 issues a label LC. The label issuing unit 23 issues a label LC by printing product information on the basis of print information output from an output unit 29 to be described below. In this embodiment, the label issuing unit 23 issues a so-called mountless label.

The control unit 20 includes an input unit 25, a storage unit 26, a calculation unit 27, a control unit 28, and an output unit 29.

The input unit 25 receives number information output from the control device 3 as an input. The input unit 25 outputs the input number information to the calculation unit 27.

The storage unit 26 stores a product master. In the product master, product related information relating to a product S is stored for each product S. The product master is a table in which a product number, a product name, a unit price, a fixed amount, and the like are associated with each other. The product master can be updated (changed).

The calculation unit 27 calculates the price of a product S. When number information output from the input unit 25 is received, the calculation unit 27 refers to the product master on the basis of a product number included in the number information. The calculation unit 27 acquires the unit price of the product S corresponding to the product number from the product master. The calculation unit 27 calculates the price of the product S on the basis of a measured value output from the measuring unit 21 and the unit price of the product. When determined information is received from the control unit 28, the calculation unit 27 determines the price and outputs print information to the label issuing unit 23. In the print information, information representing at least a product name, a weight, and price is included. The calculation unit 27 outputs display information for displaying the calculated price on the touch panel display 22a to the touch panel display 22a.

In a case in which the "print" key in the fixed key 22b of the operation unit 22 has been pressed, the control unit 28 determines the price calculated by the calculation unit 27. In a case in which it is determined that the "print" key has been pressed, the control unit 28 outputs the determined information to the output unit 29. The determined information is information used for directing determination of the price in the calculation unit 27. The output unit 29 outputs the determined information to the calculation unit 27.

Figure 4:
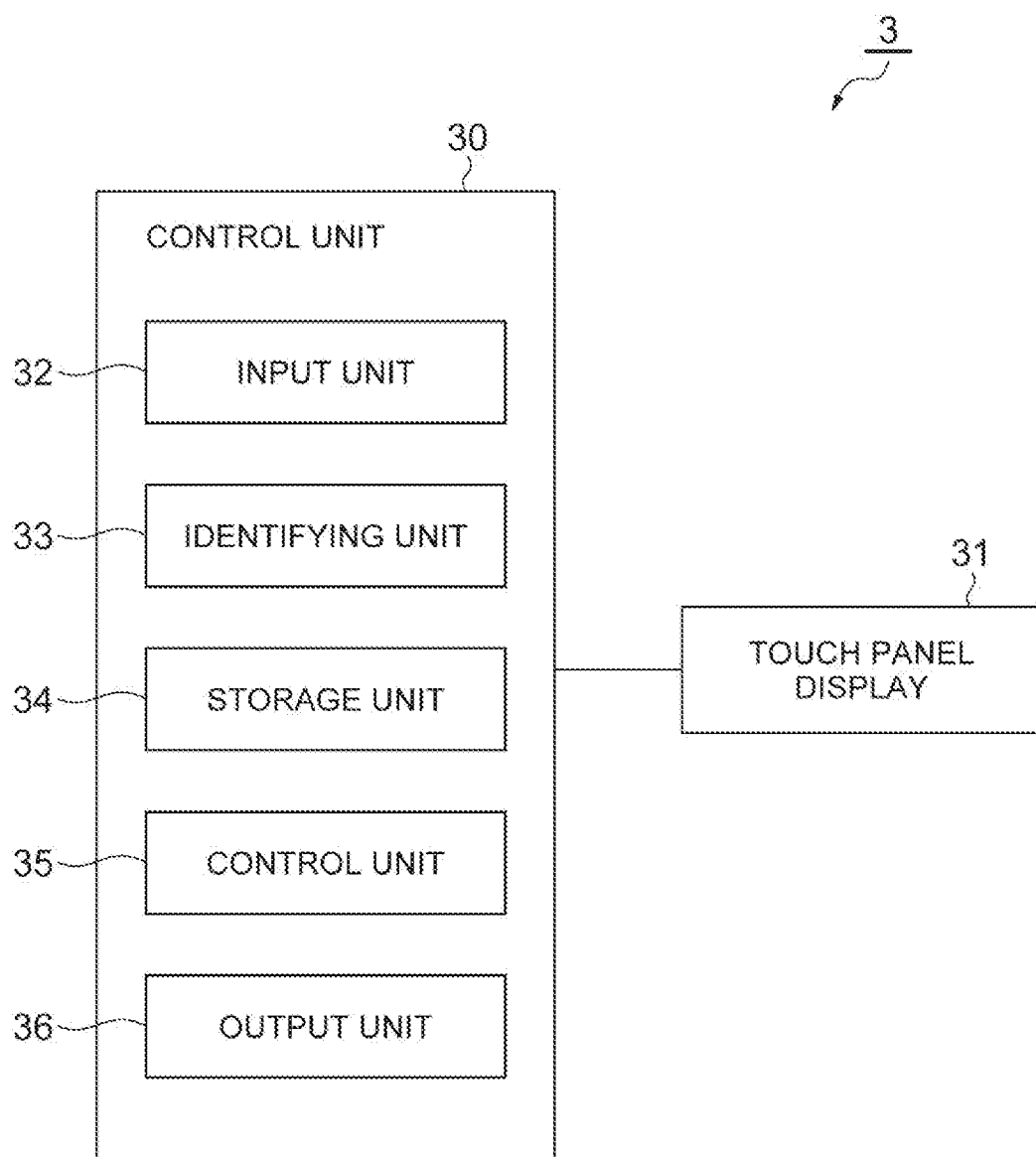
FIG. 4 is a diagram illustrating the configuration of a control device.

As illustrated in FIG. 4, the control device 3 includes a control unit 30 and a touch panel display 31. The control unit 30 controls display of the touch panel display 31. The control device 3 may be a tablet terminal acquired by integrating the control unit 30 and the touch panel display 31 or the like or may be a computer.

The control unit 30 is a part that controls various operations of the control device 3 and is configured to include a central processing unit (CPU), a read only memory (ROM), a random access memory (RAM), and the like. The control unit 30 includes an input unit 32, an identifying unit (a first acquisition unit and a second acquisition unit) 33, a storage unit 34, a control unit 35, and an output unit 36.

The input unit 32 receives image data output from the camera 5 as an input. The input unit 32 outputs the input image data to the identifying unit 33. In addition, the input unit 32 receives a learned model (an identifying model and an acquisition model) transmitted from the server 200 as an input and stores the learned model in the storage unit 34.

The identifying unit 33 identifies a kind of the product S placed in the measuring device 2 on the basis of a target image (target image data) captured by the camera 5. The identifying unit 33 detects that a product S is placed in the measurement stand 21a of the measuring device 2 on the basis of the target image data output from the input unit 32. More specifically, the identifying unit 33 detects that a product S is placed on the basis of a difference (background difference) between the target image data output from the input unit 32 and a base image (background image) stored in advance. In more details, in a case in which a degree of change in the target image data from the base image is equal to or higher than a threshold, the identifying unit 33 determines that a product S is placed.

In a case in which it is determined that the product S is placed on the stand, the identifying unit 33 determines whether or not the placement of the product S is stable. In other words, the identifying unit 33 determines whether or not the position of the product S has been set. The identifying unit 33 determines whether or not the placement of the product S is stable, for example, using an inter-frame difference method for continuous target image data. More specifically, in a case in which a difference between frames (for example, the number of pixels in which a change in the pixel value that is equal to or larger than a predetermined value has occurred) is equal to or smaller than a threshold in continuous target image data, the identifying unit 33 determines that the placement of the product S becomes stable. In a case in which it is determined that the placement of the product S becomes stable, the identifying unit 33 identifies the product S on the basis of an image of the target image data that has been determined to be stable.

Figure 5:
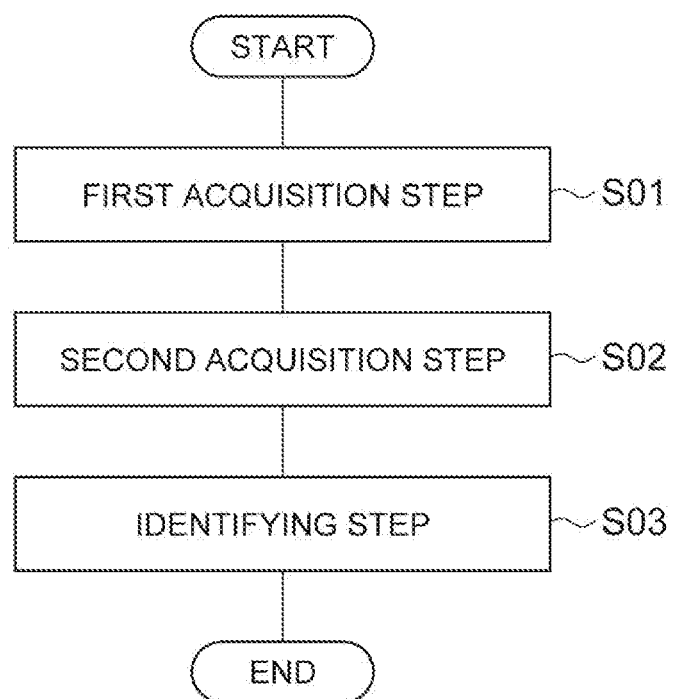
FIG. 5 is a diagram illustrating a product identifying method used in an identifying unit.

In this embodiment, the identifying unit 33 identifies a kind of the product S using an acquisition model and an identifying model. Hereinafter, a method of identifying a kind of a product S using the identifying unit 33 will be described. As illustrated in FIG. 5, the identifying unit 33 performs a first acquisition step S01, a second acquisition step S02, and an identifying step S03 as a product identifying method.

Figure 6:
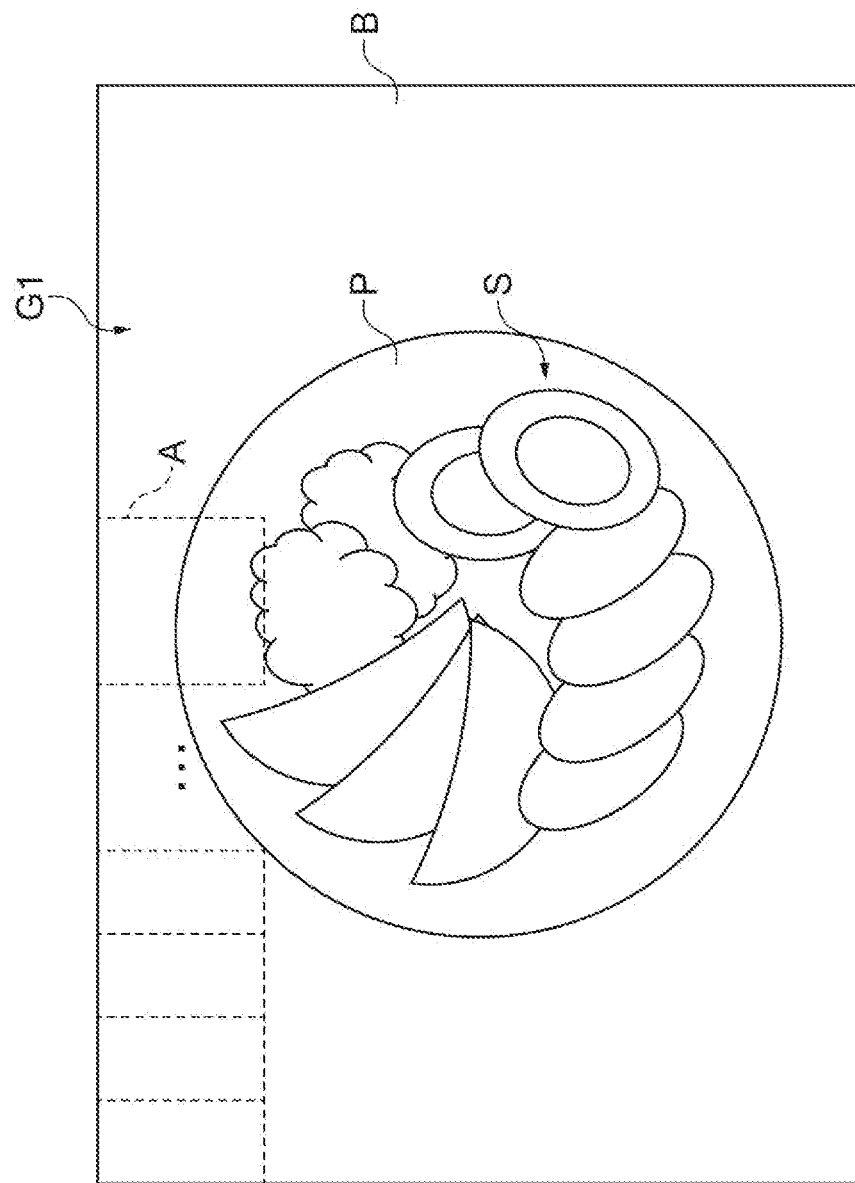
FIG. 6 is a diagram illustrating a target image including products.
Figure 7B:
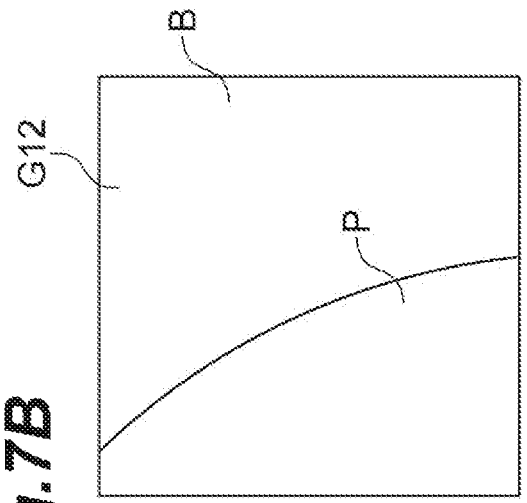
FIG. 7B is a diagram illustrating a divided target image.
Figure 7D:
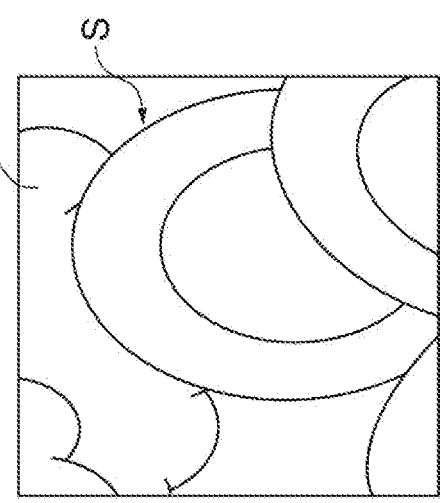
FIG. 7D is a diagram illustrating a divided target image.
Figure 7A:
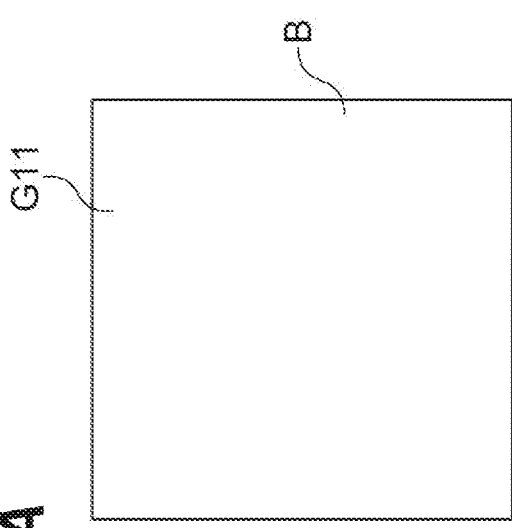
FIG. 7A is a diagram illustrating a divided target image.
Figure 7C:
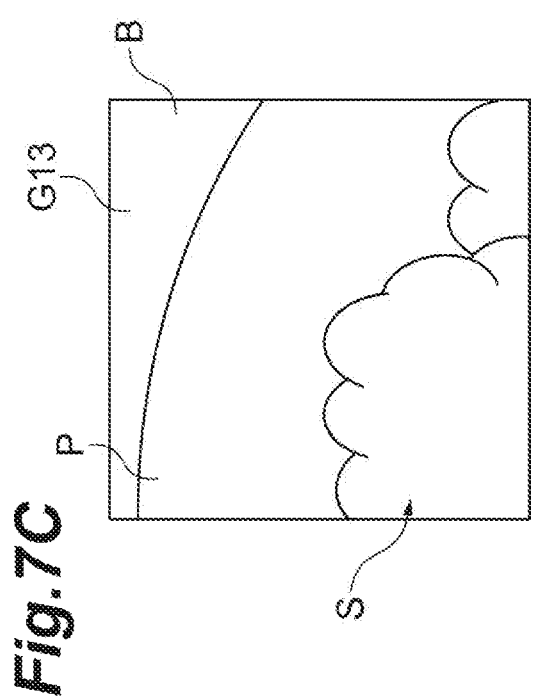
FIG. 7C is a diagram illustrating a divided target image.

The identifying unit 33 divides the target image data into a plurality of areas and acquires a plurality of divided target images (second divided images) (first acquisition step S01: FIG. 5). As illustrated in FIG. 6, the identifying unit 33 divides the target image data G1 into a plurality of areas A. More specifically, the identifying unit 33 divides target image data G1 such that areas A exhibit rectangular shapes and have the same dimensions for each of a plurality of divided target images. The identifying unit 33 divides the target image data G1 such that one divided target image and another divided target image overlap each other at least partially. In more details, the identifying unit 33 sets areas A acquired by dividing target image data G1 such that another area A moves with respect to one area A by a predetermined amount in an X direction (a first direction) that is an arrangement direction of pixels of the target image data G1 or a Y direction (a second direction that is orthogonal to the first direction). The predetermined amount is an amount corresponding to a width (½, ⅓, or the like) acquired by dividing the width of the area A in a movement direction by a natural number that is two or more. The natural number that is two or more is a value by which the number of pixels in the movement direction of the area A in the target image data G1 can be divided.

By dividing the target image data G1, as illustrated in FIGS. 7A, 7B, 7C, and 7D, the identifying unit 33 acquires divided target images G11, G12, G13, G14, and the like. The divided target image G11 is an image in which a product S and the like are not shown, in other words, only a background B is shown. The divided target image G12 is an image in which a container P and a background B are shown. The divided target image G13 is an image in which a product S, a container P, and a background B are shown. The divided target image G14 is an image in which only a product S is shown.

The identifying unit 33 acquires a plurality of divided target images satisfying a predetermined condition relating to a shown amount of the product S from among a plurality of divided target images (a second acquisition step. S02 illustrated in FIG. 5). More specifically, the identifying unit 33 acquires divided target images for which the shown amount of objects other than a product S is equal to or smaller than a threshold. In other words, the identifying unit 33 acquires divided target images for which the shown amount of a product S is larger than a threshold. The identifying unit 33 acquires divided target images for which the shown amount of objects other than a product S is equal to or smaller than a threshold in accordance with an acquisition model. The acquisition model includes a neural network NW1. The acquisition model is the same model as an extraction model to be described below.

Figure 8:
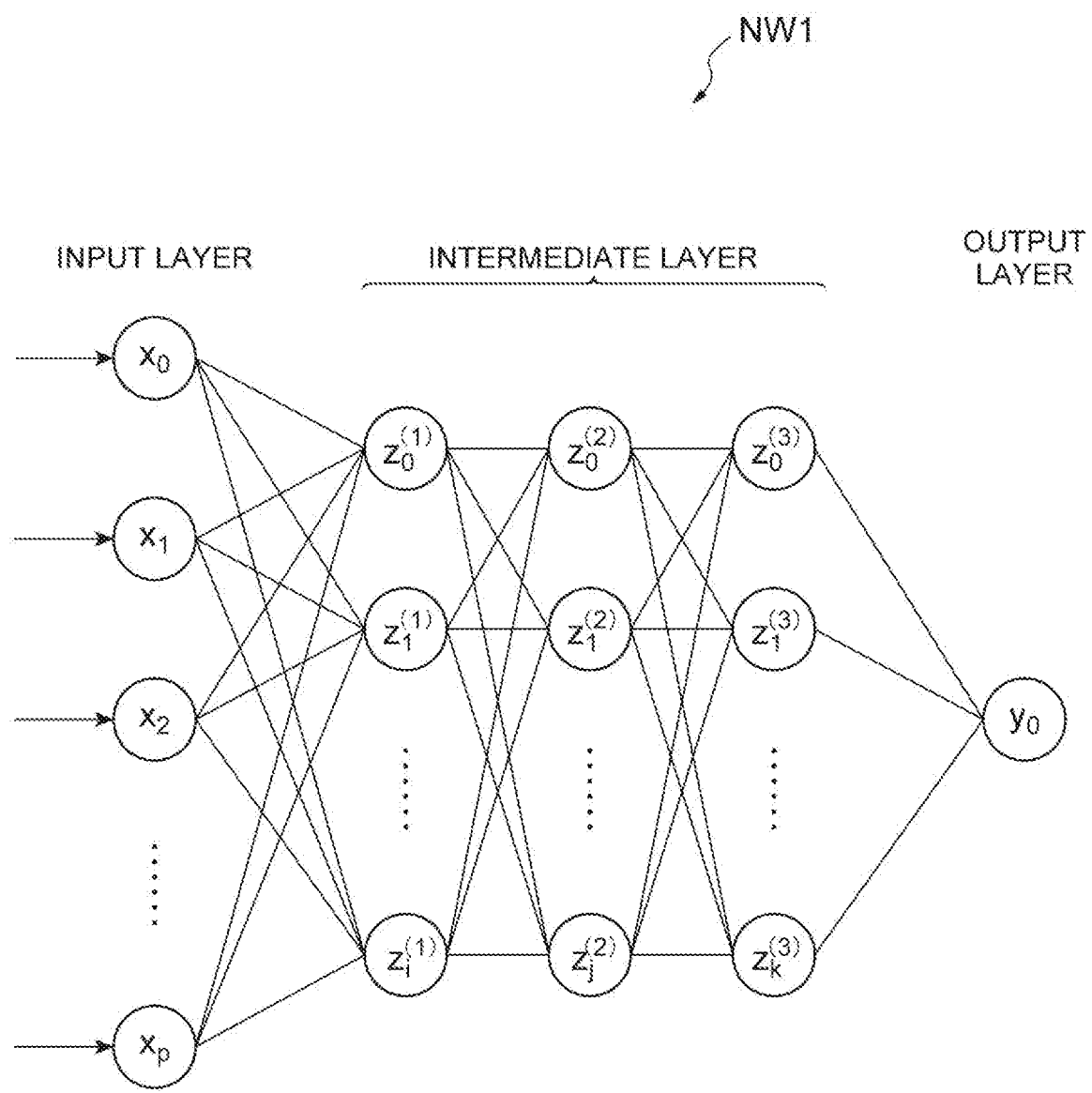
FIG. 8 is a diagram illustrating a neural network.

As illustrated in FIG. 8, the neural network NW1 of the acquisition model, for example, is composed of a first layer that is an input layer, a second layer, a third layer, and a fourth layer that are intermediate layers (hidden layers), and a fifth layer that is an output layer. The first layer directly outputs input values $x=(x0, x1, x2, \ldots, xp)$ having p parameters as elements to the second layer. Each of the second layer, the third layer, and the fourth layer converts a total input into an output and delivers the output to the next layer using an activation function. Also, the fifth layer converts a total input into an output using an activation function, and this output is an output value $y=y0$ of a neural network having one parameter as an element.

In this embodiment, the neural network NW1 receives pixel values of pixels of the divided target images G11 to G14 as inputs and outputs information representing process results. In the input layer of the neural network NW1, neurons corresponding to the number of pixels of the divided target images G11 to G14 are disposed. In the output layer of the neural network NW1, neurons used for outputting information relating to the process results are disposed. On the basis of an output value (a non-product likelihood) of neurons of the output layer, divided target images in which the shown amount of objects other than a product S is equal to or smaller than a threshold can be acquired. For example, an output value of a neuron is a value in the range of 0 to 1. In this case, a possibility of being a divided target image in which the shown amount of objects other than a product S is equal to or smaller than a threshold is represented to be low as the value of the neuron becomes larger (as the value becomes closer to "1"), and a possibility of being a divided target image in which the shown amount of objects other than a product S is equal to or smaller than the threshold is represented to be high as the value of the neuron becomes smaller (as the value becomes closer to "0"). In other words, a proportion of the occupancy of a background G and the like in a divided target image is represented to be higher in a case in which the neuron value becomes larger, and a proportion of the occupancy of a product S in the divided target image is represented to be higher in a case in which the neuron value becomes smaller. The identifying unit 33 acquires a neuron value output from the neural network NW1 and acquires a divided target image of which a neuron value is equal to smaller than a threshold.

The identifying unit 33 identifies a kind of a product S using an identifying model for a plurality of divided target images that have been acquired (identifying step S03: FIG. 5). The identifying model includes a neural network NW2.

Figure 9:
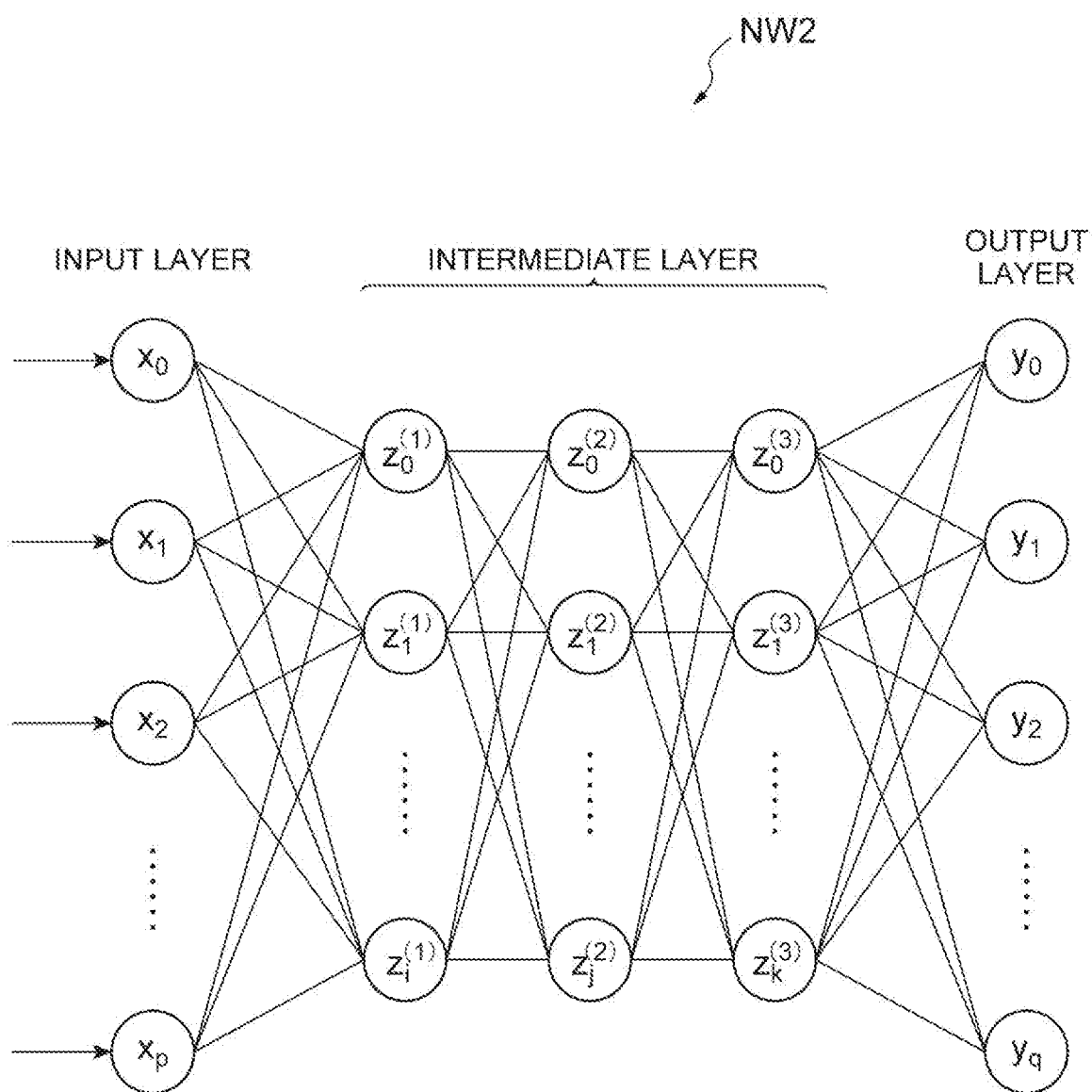
FIG. 9 is a diagram illustrating a neural network.

As illustrated in FIG. 9, the neural network NW2, for example, is composed of a first layer that is an input layer, a second layer, a third layer, and a fourth layer that are intermediate layers (hidden layers), and a fifth layer that is an output layer. The first layer directly outputs input values $x=(x0, x1, x2, \ldots, xp)$ having p parameters as elements to the second layer. Each of the second layer, the third layer, and the fourth layer converts a total input into an output and delivers the output to the next layer using an activation function. Also, the fifth layer converts a total input into an output using an activation function, and this output is an output value $y=(y0, y1, \ldots, yq)$ of the neural network NW2 having q parameters as elements.

In this embodiment, the neural network NW2 receives pixel values of pixels of each divided target image as inputs and outputs information representing an identification result of a product S for each divided target image. In the input layer of the neural network NW2, neurons corresponding to the number of pixels of an image are disposed. In the output layer of the neural network NW2, a neuron used for outputting information relating to an identification result of a product S is disposed. A kind of the product S can be identified on the basis of an output value (a product likelihood) of the neuron of the output layer. An output value y corresponds to a product likelihood of the product S. For example, an output value $y_1$ corresponds to a product likelihood of a product $S_1$, and an output value $y_1$ corresponds to a product likelihood of a product $S_1$. For example, an output value of a neuron is a value in the range of 0 to 1. For example, the product likelihood of the product $S_1$ is "0.8" in a case in which the value of the output value $y_1$ is "0.8", and the product likelihood of the product $S_2$ is "0.2" in a case in which the value of the output value $y_2$ is "0.2". In this case, the possibility of being a product S of the target image data G1 is represented to be higher as the value of the neuron becomes larger (as the value becomes closer to "1"), and the possibility of being the product S of the target image data G1 is represented to be lower as the value of the neuron becomes smaller (as the value becomes closer to "0"). In other words, the possibility of being the product S is represented to be high in a case in which the neuron value becomes large, and the possibility of being the product S is represented to be low in a case in which the neuron value becomes small.

The identifying unit 33 inputs the divided target image to the identifying model. In accordance with the input of a divided target image to the neural network NW2 of the identifying model, the identifying unit 33 acquires an identification result including an output value output from the neural network NW2 for each divided target image. In the identification result, all kinds of products registered in the product master are included.

The identifying unit 33 ranks candidate products on the basis of the identification result. More specifically, the identifying unit 33 performs weighting on the basis of the magnitude of the neuron value of each divided target image and ranks products on the basis of majority decision of weightings assigned in the identification result. The identifying unit 33 generates identification information in which a product number and a rank are associated with each other for all kinds of products. The identifying unit 33 outputs the image information of the image data used for the identifying process and the identification information to the control unit 35.

When the image information and the identification information are output from the identifying unit 33, the control unit 35 causes the touch panel display 31 to display the image information and the identification information. The control unit 35 controls the display of the touch panel display 31 on the basis of an input accepted by the touch panel display 31. More specifically, the control unit 35 causes an image of the product S based on the image information to be displayed on one screen displayed by the touch panel display 31. The control unit 35 displays product names of products having high ranks among candidates for products in the identification information on one screen. The control unit 35 outputs number information representing a product number to the output unit 36 on the basis of the identification information or the input accepted by the touch panel display 31. The output unit 36 outputs the number information to the measuring device 2.

The storage unit 34 stores a product master. This product master is configured to include the same details as those of the product master stored in the storage unit 26 of the measuring device 2. The storage unit 34 stores a learned model.

As illustrated in FIG. 1, the server 200 includes a communication unit 201 and a learned model generating unit (an acquisition unit, a dividing unit, an extraction unit, and a generation unit) 202. The server 200 is an apparatus that generates a learned model using machine learning. The server 200 is composed of a central processing unit (CPU), a read only memory (ROM), a random access memory (RAM), and the like.

The communication unit 201 communicates with the measuring device 100. The communication unit 201 receives image data transmitted from the measuring device 100 and outputs the received image data to the learned model generating unit 202. The communication unit 201 transmits the learned model output from the learned model generating unit 202 to the measuring device 100.

The learned model generating unit 202 acquires learning data used for machine learning and generates a learned model by performing machine learning using the acquired learning data. In this embodiment, the learning data is a teacher image. The teacher image, for example, is image data acquired by the camera 5 of the measuring device 100.

Figure 10:
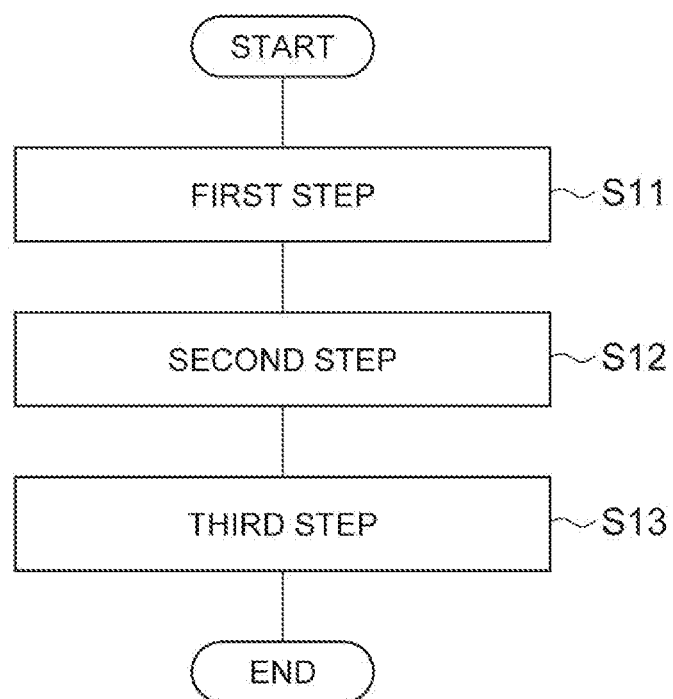
FIG. 10 is a diagram illustrating a method of generating an extraction model according to a learned model generating unit.

The learned model generating unit 202 generates an extraction model and an identifying model. First, a method of generating an extraction model will be described. The extraction model is a model that is the same as the acquisition model described above. The extraction model is generated using machine learning based on images not including a product. Hereinafter, a method of generating an extraction model using the learned model generating unit 202 will be described. As illustrated in FIG. 10, the learned model generating unit 202 performs a first step S11, a second step S12, and a third step S13 as a method of generating an extraction model.

Figure 11:
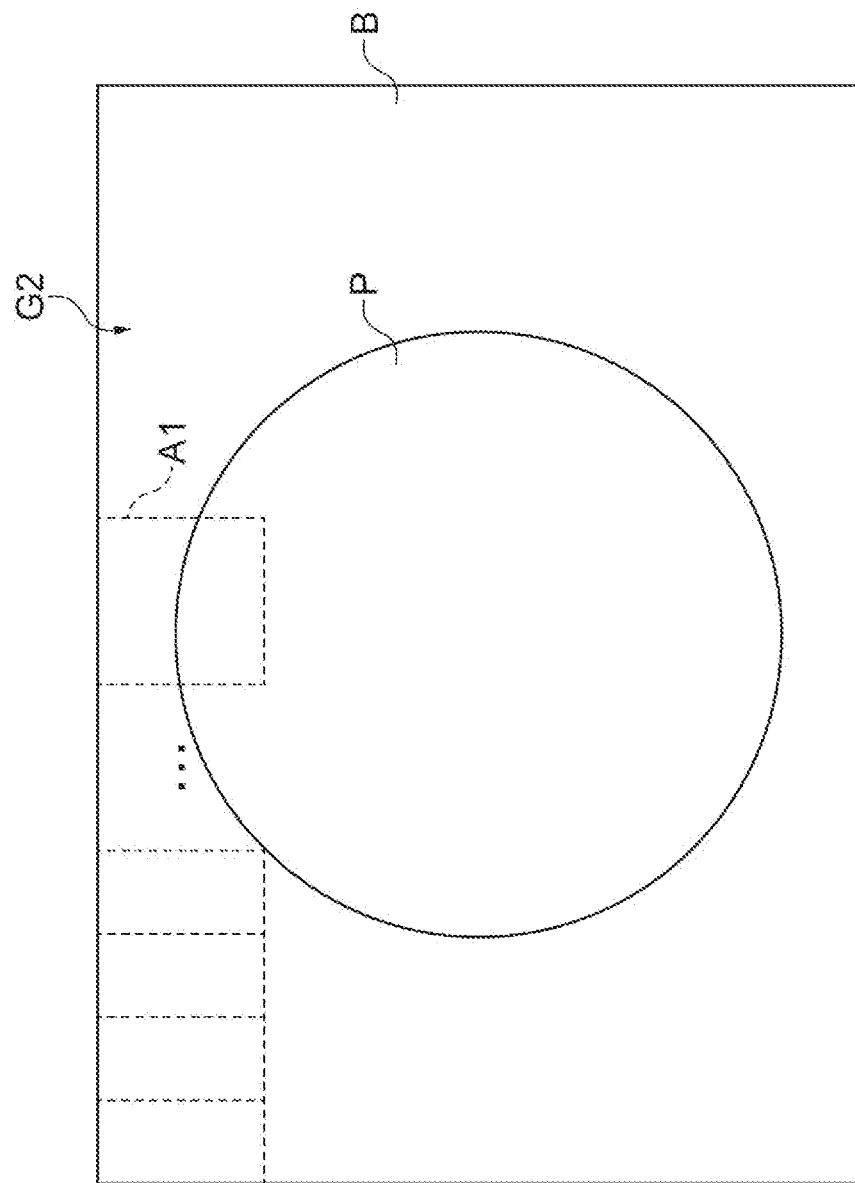
FIG. 11 is a diagram illustrating a non-product image not including a product.

The learned model generating unit 202 acquires a non-product image not including a product as a teacher image (first step S11 illustrated in FIG. 10). A background B and a container P may be included in the non-product image. The learned model generating unit 202 divides the non-product image into a plurality of areas, thereby acquiring a plurality of non-product divided images (second step S12 illustrated in FIG. 10). As illustrated in FIG. 11, the learned model generating unit 202 divides non-product image data G2 into a plurality of areas A1. More specifically, the learned model generating unit 202 divides the non-product image data G2 such that areas A1 exhibit rectangular shapes and have the same dimension for each of the plurality of non-product divided images. The learned model generating unit 202 divides the non-product image data G2 such that one non-product divided image and another non-product divided image overlap each other at least partially. In more details, the learned model generating unit 202 sets areas A1 acquired by dividing the non-product image data G2 such that another area A1 moves with respect to one area A1 by a predetermined amount in an X direction or a Y direction that is an arrangement direction of pixels of the non-product image data G2. The predetermined amount is an amount corresponding to a width acquired by dividing the width of the area A1 in a movement direction by a natural number that is two or more. The natural number that is two or more is a value by which the number of pixels in the movement direction of the area A1 in the non-product image data G2 can be divided.

The learned model generating unit 202 performs machine learning on the basis of a plurality of non-product divided images that have been acquired, thereby generating an extraction model (a third step S13 illustrated in FIG. 10). The machine learning can be performed using a known machine learning algorithm. The extraction model includes a neural network NW1 (see FIG. 8).

Figure 12:
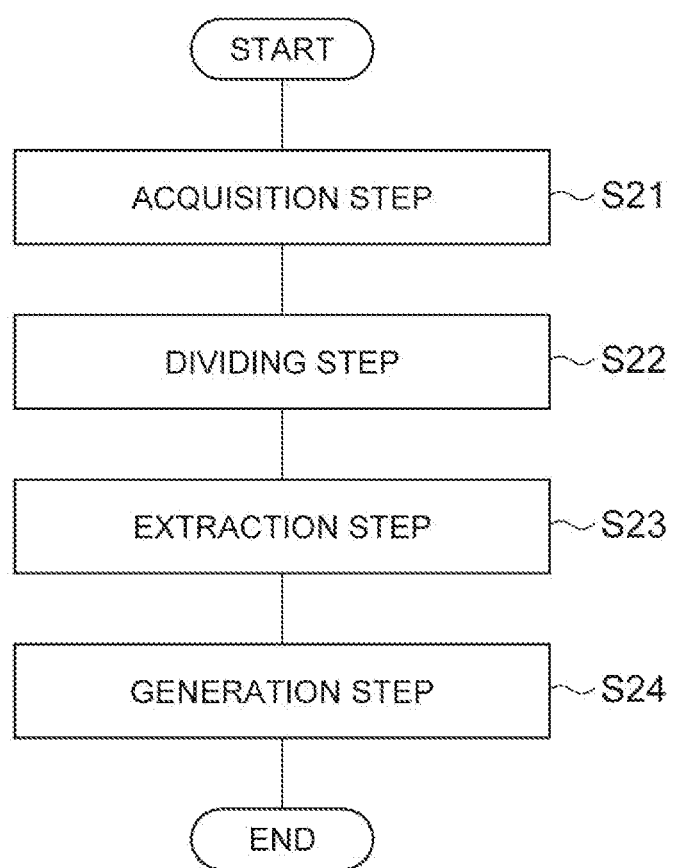
FIG. 12 is a diagram illustrating a method of generating an identifying model according to a learned model generating unit.

The learned model generating unit 202 generates an identifying model using the extraction model. Hereinafter, a method of generating an identifying model (a learned model generating method) using the learned model generating unit 202 will be described. As illustrated in FIG. 12, the learned model generating unit 202 performs an acquisition step S21, a dividing step S22, an extraction step S23, and a generation step S24 as a method of generating an identifying model.

The learned model generating unit 202 acquires a product image and product information relating to a kind of product (an acquisition step S21 illustrated in FIG. 12). The learned model generating unit 202, for example, acquires product image data acquired by the camera 5 and product information representing a kind of product (for example, salads) included in the product image data. The product information corresponds to information included in the product master described above and includes a product number, a product name, and the like. In addition, the product image may be a sample image or the like other than the image data acquired by the camera 5.

Figure 13:
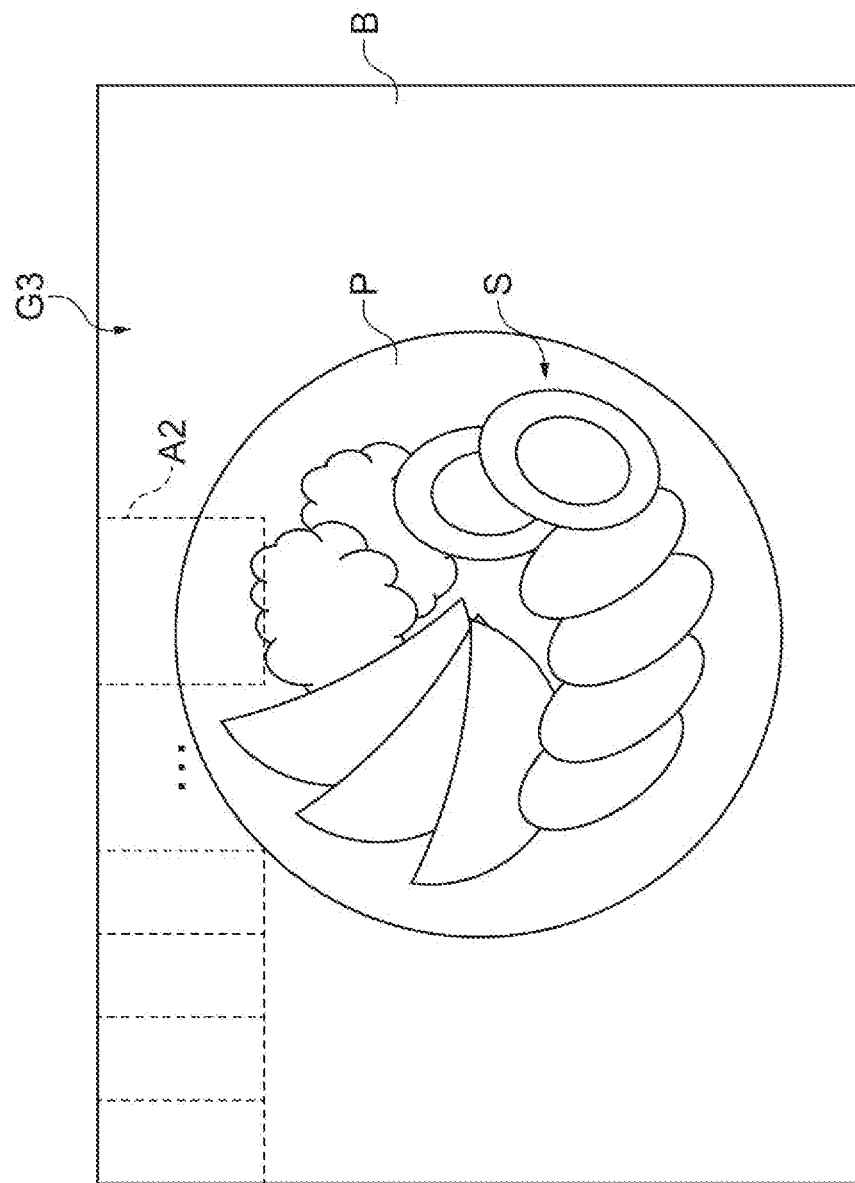
FIG. 13 is a diagram illustrating a product image including products.
Figure 14A:
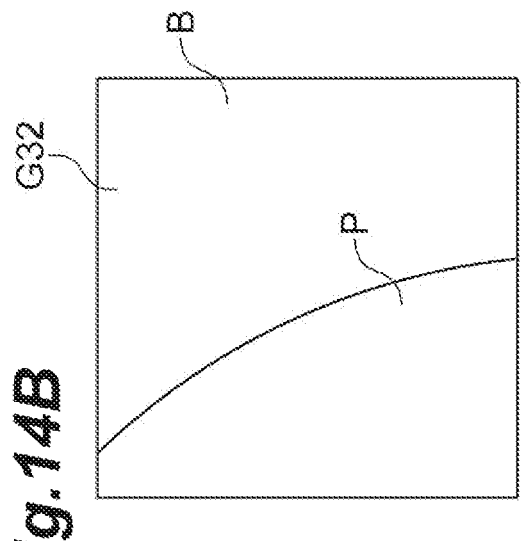
FIG. 14A is a diagram illustrating a divided image.
Figure 14B:
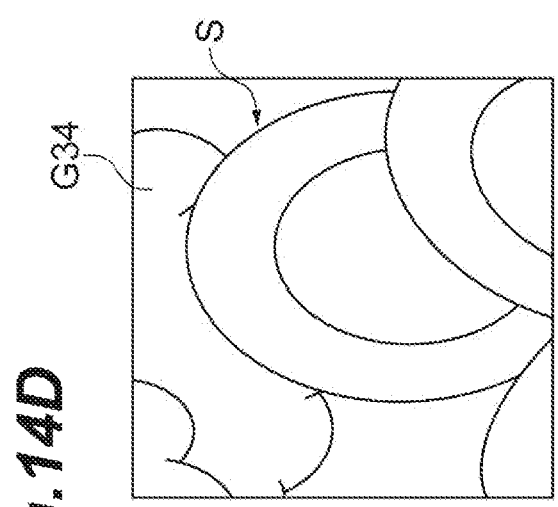
FIG. 14B is a diagram illustrating a divided image.
Figure 14C:
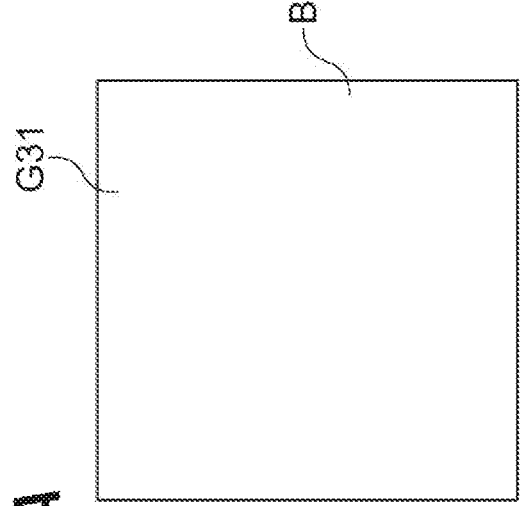
FIG. 14C is a diagram illustrating a divided image.
Figure 14D:
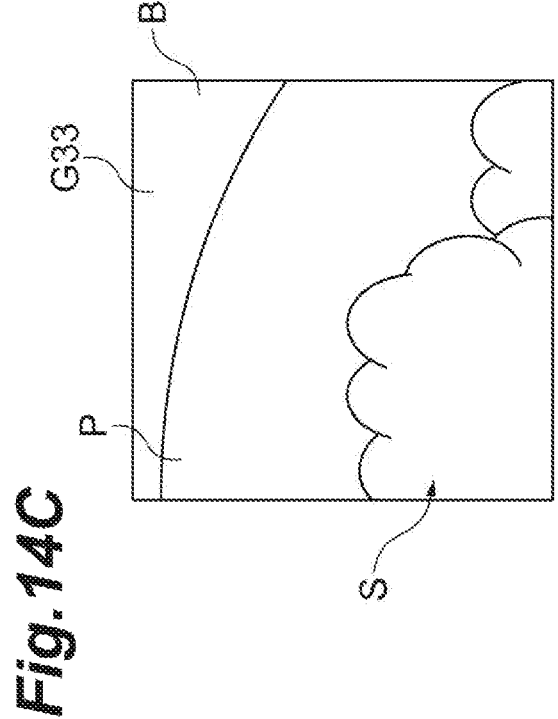
FIG. 14D is a diagram illustrating a divided image.

The learned model generating unit 202 acquires a plurality of divided images (first divided images) by dividing the product image data into a plurality of areas (a dividing step S22 illustrated in FIG. 12). As illustrated in FIG. 13, the learned model generating unit 202 divides product image data G3 into a plurality of areas A2. More specifically, the learned model generating unit 202 divides the product image data G3 such that the areas A2 exhibit rectangular shapes and have the same dimensions for each of a plurality of divided images. The learned model generating unit 202 divides the product image data G3 such that the areas A2 and the areas A1 have the same shapes and the same dimensions. The learned model generating unit 202 divides the product image data G3 such that one divided image and another divided image overlap each other at least partially. In more details, the learned model generating unit 202 sets the areas A2 acquired by dividing the product image data G3 such that another area A2 moves with respect to one area A2 by a predetermined amount in an X direction or a Y direction that is an arrangement direction of pixels of the product image data G3. The predetermined amount is an amount corresponding to a width acquired by dividing the width of the area A in a movement direction by a natural number that is two or more. The natural number that is two or more is a value by which the number of pixels in the movement direction of the area A in the product image data G3 can be divided.

By dividing the product image data G3, the learned model generating unit 202, as illustrated in FIGS. 14A, 14B, 14C, and 14D, acquires divided images G31, G32, G33, G34, and the like. The divided image G31 is an image in which a product S and the like are not shown, in other words, only a background B is shown. The divided image G32 is an image in which a container P and a background B are shown. The divided image G33 is an image in which a product S, a container P, and a background B are shown. The divided image G34 is an image in which only a product S is shown.

The learned model generating unit 202 acquires a plurality of divided images that satisfy a predetermined condition relating to the shown amount of the product S among the plurality of divided images (an extraction step S23). More specifically, the learned model generating unit 202 acquires divided images of which the shown amount of objects other than the product S is equal to or smaller than a threshold. In other words, the learned model generating unit 202 acquires divided images of which the shown amount of the product S is larger than a threshold. The learned model generating unit 202 acquires divided images of which the shown amount of objects other than the product S is equal to or smaller than a threshold using the extraction model. The learned model generating unit 202 acquires a neuron value output from a neural network of the extraction model and acquires divided images of which the neuron value is equal to or smaller than a threshold. The learned model generating unit 202 associates the acquired divided images with product information (a kind of product (a product name, a product number, and the like)). In other words, the learned model generating unit 202 labels the acquired divided images with product information.

The learned model generating unit 202 performs machine learning by associating the plurality of extracted divided images with product information, thereby generating an identifying model (a generation step S24 illustrated in FIG. 12). The machine learning can be performed using a known machine learning algorithm. The learned model generating unit 202, as illustrated in FIG. 9, generates an identifying model including a neural network NW2. The identifying model may include a convolutional neural network. In addition, the identifying model may include a neural network of a plurality of layers (for example, eight layers or more). In other words, an identifying model may be generated through deep learning. The learned model generating unit 202 outputs the acquisition model (the extraction model) and the identifying model to the communication unit 201 at a predetermined timing.

As described above, the measuring system 1 according to this embodiment includes the server 200 that generates an identifying model used for identifying a kind of product from a product image in which a product is included and the measuring device 100 that identifies a kind of product from a target image in which the product is included. The server 200 includes the learned model generating unit 202. The learned model generating unit 202 acquires a product image and product information relating to a kind of the product (an acquisition step) and acquires a plurality of divided images by dividing the product image into a plurality of areas (a dividing step). The learned model generating unit 202 extracts a plurality of divided images satisfying a predetermined condition relating to the shown amount of a product among the plurality of divided images (an extraction step). The learned model generating unit 202 performs machine learning by associating a plurality of extracted divided images with product information, thereby generating an identifying model (a generation step).

In this way, in the measuring system 1 according to this embodiment, the learned model generating unit 202 of the server 200 extracts a plurality of divided images satisfying a predetermined condition relating to the shown amount of a product among the plurality of divided images. The divided images include an image in which only a product is shown, an image in which a product and objects other than a product (a container, a background, and the like) are shown, and an image in which only objects other than a product are shown. The learned model generating unit 202 extracts divided images satisfying a predetermined condition among such divided images and performs machine learning on the basis of the extracted divided images. In accordance with this, the learned model generating unit 202 can perform machine learning based on appropriate teacher images. Accordingly, the server 200 can generate an identifying model achieving an improved accuracy of identification of a product.

In addition, in the measuring system 1 according to this embodiment, the control device 3 includes the identifying unit 33. The identifying unit 33 acquires a plurality of divided target images by dividing a target image into a plurality of areas (a first acquisition step) and acquires a plurality of divided target images satisfying a predetermined condition relating to the shown amount of a product among the plurality of divided target images (a second acquisition step). The identifying unit 33 acquires a process result acquired by performing a process using an identifying model for the plurality of divided target images that have been acquired and identifies a kind of product on the basis of the process result (an identifying step).

In this way, in the measuring system 1 according to this embodiment, the identifying unit 33 of the control device 3 extracts a plurality of divided target images satisfying a predetermined condition relating to the shown amount of a product among a plurality of divided target images. The identifying unit 33 acquires divided target images satisfying a predetermined condition among divided target images and performs a process using an identifying model for the acquired divided target images. In accordance with this, the measuring device 100 can perform a process based on appropriate divided target images. Accordingly, the measuring system 1 achieves improvement of an accuracy of identification of a product.

In the measuring system 1 according to this embodiment, the learned model generating unit 202 of the server 200 extracts divided images in which the shown amount of objects other than a product is equal to or smaller than a threshold. In other words, the learned model generating unit 202 extracts divided images in which the shown amount of a product is equal to or larger than a threshold. In this method, divided images in which a product occupancy rate is high are extracted. In other words, the measuring system 1 can exclude divided images in which a container and a background other than a product are shown. For this reason, the measuring system 1 can perform machine learning using divided images in which a product is shown. Accordingly, the measuring system 1 can generate an identifying model that achieves an improved accuracy of identification of a product.

In the measuring system 1 according to this embodiment, by using an extraction model generated through machine learning based on images not including a product, the learned model generating unit 202 acquires a neuron value representing a likelihood of being a divided image not including a product for each of a plurality of divided images and extracts divided images of which a neuron value is equal to or smaller than a threshold. In this method, only divided images in which a product is shown can be appropriately extracted.

In the measuring system 1 according to this embodiment, the learned model generating unit 202 acquires a non-product image not including a product and acquires a plurality of non-product divided images by dividing a non-product image into a plurality of areas. The learned model generating unit 202 performs machine leaning on the basis of a plurality of non-product divided images, thereby generating an extraction model. In accordance with this, the measuring system 1 can appropriately generate an extraction model.

More specifically, in the measuring system 1 according to this embodiment, the learned model generating unit 202 divides a product image such that areas exhibit rectangular shapes and have the same dimensions for each of a plurality of divided images. The learned model generating unit 202 divides a non-product image such that a divided image has the same shape and the same dimension as those of the divided image for each of a plurality of non-product divided image. In this method, since the divided image and the non-product divided image have the same shapes and the same dimensions, a conversion process for converting the shape and the size of an image does not need to be performed. Therefore, in the measuring system 1, reduction in the process load is achieved.

In the measuring system 1 according to this embodiment, the learned model generating unit 202 divides a product image such that one divided image and another divided image overlap each other at least partially. In this method, when a product image is divided, even in a case in which one product included in products is broken in one divided image, there are cases in which the entirety of one product enters another divided image. For this reason, in the measuring system 1, since machine learning based on appropriate teacher images can be performed, an identifying model having an improved product identifying accuracy can be generated.

In the measuring system 1 according to this embodiment, the learned model generating unit 202 sets areas acquired by dividing a product image such that another area moves by a predetermined amount with respect to one area in the X direction that is the arrangement direction of pixels of the product image or the Y direction. In this method, by moving the area by a predetermined amount, the product image can be divided such that each pixel is included in each of areas aligned in the movement direction the same number of times.

In the measuring system 1 according to this embodiment, the learned model generating unit 202 divides a product image such that areas exhibit rectangular shapes and have the same dimensions for each of a plurality of divided images. In this method, since all the divided images have the same shapes and the same dimensions, a conversion process for converting the shape and the size of the images does not need to be performed. Therefore, the measuring system 1 can reduce the process load.

In the measuring system 1 according to this embodiment, the identifying unit 33 acquires divided target images of which the shown amounts of objects other than a product are equal to or smaller than a threshold. In this method, images having high product occupancy rates are acquired. In other words, images in which a container and a background other than a product are shown can be excluded. For this reason, the measuring system 1 can improve an accuracy of identification of a product.

In the measuring system 1 according to this embodiment, by using an acquisition model generated through machine learning based on images not including a product, the identifying unit 33 acquires a neuron value representing a likelihood of being a divided target image not including a product for each of a plurality of divided target images and acquires divided target images of which neuron values are equal to or smaller than a threshold. In this method, only divided target images in which a product is shown can be appropriately acquired.

In the measuring system 1 according to this embodiment, the identifying unit 33 acquires a plurality of process results by performing a process using an identifying model for each of a plurality of divided target images and identifies a kind of product based on the plurality of process results. In this method, the process using the identifying model is performed for individual divided target images, and a plurality of process results are acquired, whereby the accuracy of identification of a product can be further improved.

In the measuring system 1 according this embodiment, the identifying unit 33 performs weighting for the process result on the basis of a degree of a neuron value representing a likelihood of a product being one kind and identifies a kind of the product on the basis of majority decision of weightings assigned to the process result. In this method, a product can be identified with a higher accuracy.

In the measuring system 1 according to this embodiment, the identifying unit 33 divides a target image such that areas exhibit rectangular shapes and have all the same dimensions for each of a plurality of divided target images. In this method, since all the divided target images have the same shapes and the same dimensions, a conversion process for converting the shape and the size of an image does not need to be performed. Therefore, the measuring system 1 can reduce the process load.

As above, although an embodiment of the present invention has been described, the present invention is not necessarily limited to the embodiment described above, and various changes can be made in a range not departing from the concept thereof.

Figure 15:
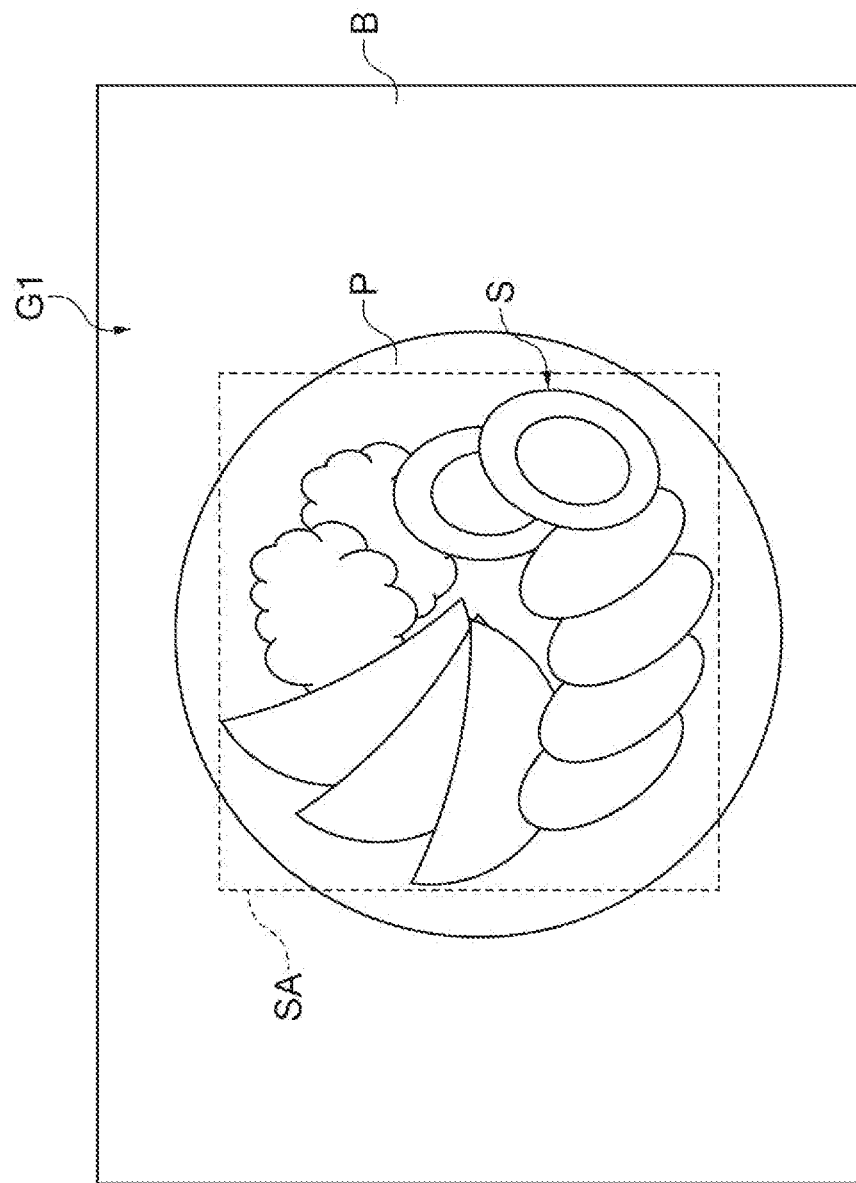
FIG. 15 is a diagram illustrating a target image including products.

In the embodiment described above, a form in which the identifying unit 33 divides a target image data G1 into a plurality of areas A has been described as one example. However, the identifying unit 33 may acquire a plurality of divided images by comparing a product image with a base image not including a product, cutting a product area, in which the entire product is included, smaller than a product image from the product image (a cutting step), dividing the product area into a plurality of areas. More specifically, as illustrated in FIG. 15, the identifying unit 33 compares target image data G1 that is a product image with a base image and cuts a product area SA in which a product S is minimally included from the target image data G1. The base image is an image in which only a background B is shown. The identifying unit 33 acquires a plurality of divided images by dividing the product area SA into a plurality of areas. In this method, since a product area SA acquired by excluding parts other than the product S from the target image data G1 is divided, an unnecessary area does not need to be divided. Therefore, the process load can be reduced.

In the embodiment described above, a form in which, in order for the identifying unit 33 to set areas A acquired by dividing target image data G1, a predetermined amount by which another area A is moved with respect to one area A is an amount corresponding to a width (½, ⅓, or the like) acquired by dividing the width of the area A in the movement direction by a natural number that is two or more has been described as one example. However, the identifying unit 33 may set the predetermined amount as one pixel. In other words, the identifying unit 33 may set areas acquired by dividing target image data G1 such that another area A in an X direction or a Y direction, which is an arrangement direction of pixels of the target image data G1, is moved by one pixel with respect to one area A. This similarly applies also to a case in which the learned model generating unit 202 sets areas A1 acquired by dividing the non-product image data G2 and a case in which areas A2 acquired by dividing the product image data G3 are set.

In the embodiment described above, a form in which the neural network NW2 of the identifying model receives a pixel value of each pixel of each divided target image as an input and outputs information representing an identification result of a product S for each divided target image has been described as one example. However, the identifying model may be configured to include the neural network NW2 that receives a pixel value of each pixel of each divided target image as an input and outputs information representing an identification result of a product S for each pixel.

In the embodiment described above, a form in which the identifying unit 33 performs weighting on the basis of the magnitude of a neuron value of each divided target image and ranks products on the basis of majority decision of weightings assigned to an identification result has been described as one example. However, a different method may be used for the identifying unit 33 to rank (identify) products. For example, the identifying unit 33 may rank products using only neuron values that are equal to or larger than a threshold or may rank products by employing an identification result of a divided target image of an area of a center part of the target image data with priority. In addition, the identifying unit 33 may not employ neuron values (product likelihoods that are equal to or smaller than a threshold) that are equal to or smaller than a threshold among neuron values of each divided target image.

Furthermore, for example, in a case in which a neuron value (output value) $y_2$ (a product likelihood of being a product $S_2$) of one divided target image is "0.9", a neuron value $y_2$ of another divided target image is "0.4", and a neuron value $y_5$ (a product likelihood of being a product $S_5$) of the one divided target image described above is "0.7", and dispersion of neuron values relating to the product $S_2$ is large, the identifying unit 33 may set a weighting of the product $S_2$ to be low. In other words, in a case in which there is a difference (deviation) between a neuron value corresponding to one product of one divided target image and a neuron value corresponding to one product of another divided target image (there is dispersion in the neuron value), and a neuron value corresponding to another product of one divided target image is larger than a predetermined value, the identifying unit 33 sets the weighting of the one product to be low.

In the embodiment described above, a form in which the identifying unit 33 acquires divided target images of which the shown amounts of objects other than a product are equal to or smaller than a threshold are acquired among a plurality of divided target images using an acquisition model has been described as one example. However, the identifying unit 33 may extract divided target images of which pixel inclusion ratios are equal to or lower than a predetermined threshold among a plurality of divided target images on the basis of feature quantities of pixels of an image in which the product is not included. In this method, only divided target images in which a product is shown can be appropriately extracted without using an acquisition model.

In the embodiment described above, a form in which the identifying unit 33 acquires divided target images in which the shown amount of objects other than a product is equal to or smaller than a threshold has been described as one example. However, the identifying unit 33 may acquire inclusion/non-inclusion of shown objects other than a product (a container, a background, and the like) in an outer edge portion (outer edge area) of a divided target image and acquire the divided target image in a case in which there is no inclusion of shown objects other than a product. In accordance with this, a divided target image having a high product occupancy rate can be extracted.

In the embodiment described above, a form in which one product S is included in target image data, and the identifying unit 33 identifies a kind of one product S has been described as one example. However, a plurality of products may be included in the target image data. In such a case, the identifying unit 33 identifies a kind of each of the plurality of products. More specifically, the identifying unit 33 extracts contour lines (edges) on the basis of a difference between target image data and a base image stored in advance and acquires an area in which a product is included on the basis of the edges. At this time, even when there are two or more products, there are cases in which one area is acquired in accordance with a situation in which the products overlap each other in a part or the like. For this reason, for example, the identifying unit 33 compares the area with the area of the container and acquires an area of each product (divides an area for each product). As a method for acquiring an area of each product, a different method may be used. When a plurality of areas are acquired, the identifying unit 33 identifies a kind of product for each area.

In addition, for example, in a case in which a plurality of products are loaded on one dish or the like, the identifying unit 33 identifies kinds of a plurality of products in accordance with the following process. The identifying unit 33 takes majority decision of process results of one divided target image and a plurality of divided target images near the one divided target image and sets a result thereof as a result (a kind of products) at the center coordinates of an area including the one divided target image and the plurality of divided target images (process results of the divided target images are smoothed). The identifying unit 33 performs the process described above for all the divided target images and acquires a result at the center coordinates of each area. The identifying unit 33 identifies a kind of each of the plurality of products by unifying areas in which the same results (products) are in close formation among the acquired results as one. In addition, in a case in which a plurality of products are included, unlike in the embodiment described above, the measuring device 100 is used not as an apparatus performing selling by measure but a product identifying device. For example, in a case in which a plurality of foods are placed on a tray, the product identifying device may identify a kind of each of the plurality of foods or inspect contents of a lunch box.

In the embodiment described above, a form in which the learned model generating unit 202 divides a product image such that all the areas exhibit rectangular shapes and have the same dimensions for a plurality of divided images and divides a non-product image such that an area has the same shape and the same dimension as those of a divided image for each of a plurality of non-product divided images has been described as one example. However, there may be differences in the shapes and the dimensions between a product image and a non-product divided image. For example, a divided image may have resolution higher than that of a non-product divided image. In such a case, in a case in which the shape is set to a rectangular shape, it is preferable to uniformize ratios between vertical and horizontal lengths (aspect ratios). In other words, it is preferable that a divided image and a non-product divided image are similar figures. In accordance with this, a process for converting the ratio of images does not need to be performed, and accordingly, the process load is reduced.

In the embodiment described above, a form in which the learned model generating unit 202 acquires divided images in which the shown amount of objects other than a product is equal to or smaller than a threshold among a plurality of divided images using the extraction model has been described as one example. However, the learned model generating unit 202 may extract divided images of which pixel inclusion ratios are equal to or lower than a predetermined threshold among a plurality of divided images on the basis of feature quantities of pixels of an image not including a product. In this method, only divided images in which a product is shown can be appropriately extracted without using an extraction model.

In the embodiment described above, a form in which the learned model generating unit 202 acquires divided images in which the shown amount of objects other than a product is equal to or smaller than a threshold has been described as one example. However, the learned model generating unit 202 may acquire presence/absence of showing of objects other than a product (a container, a background, and the like) in an outer edge portion (an outer edge area) of a divided image and acquire the divided image in a case in which there is no showing of objects other than a product. In accordance with this, divided images having high product occupancy rates can be extracted.

In the embodiment described above, a form in which the learned model generating unit 202 acquires a plurality of divided images satisfying a predetermined condition relating to the shown amount of a product S among a plurality of divided images and generates an identifying model by performing machine learning by associating the plurality of extracted divided images with product information has been described as one example. However, the learned model generating unit 202 may extract one divided image in which the shown amount of objects other than a product is equal to or smaller than a threshold and other divided images in which the shown amount of objects other than a product is larger than a threshold from among a plurality of divided images and generate an identifying model by performing machine learning on the basis of the one divided image and the other divided images that have been extracted by associating the one divided image with product information and associating the other divided images with non-product information indicating an object other than a product. The identifying unit 33 extracts other divided images in which the shown amount of objects other than a product is larger than a threshold (the shown amount of a product is equal to or smaller than a threshold), for example, using an extraction model.

More specifically, the learned model generating unit 202 acquires a neuron value output from a neural network of the extraction model and extracts one divided image in which the shown amount of objects other than a product S is equal to or smaller than a threshold and other divided images in which the shown amount of objects other than the product is equal to or larger than a threshold on the basis of the neuron value. In other words, the learned model generating unit 202 classifies one divided image in which the shown amount of objects other than a product S is equal to or smaller than a threshold and other divided images in which the shown amount of objects other than the product is larger than a threshold and extracts the one divided image and the other divided images. The learned model generating unit 202 labels the one divided image with product information (a product name) and labels the other divided images with a non-product information indicating an object other than the product (a background, a container, and the like). The learned model generating unit 202 performs machine learning on the basis of the one divided image and the other divided images, thereby generating an identifying model. The machine learning can be performs using a known machine learning algorithm.

In the embodiment described above, a form in which the identifying unit 33 acquires a plurality of divided target images satisfying a predetermined condition relating to the shown amount of a product S among a plurality of divided target images, acquires a process result acquired by performing the process using the identifying model by inputting the divided target images to the identifying model, and identifies a kind of the product S on the basis of the process result has been described as one example. However, the identifying unit 33 may divide target image data into a plurality of areas (a divided image acquiring step) and input a plurality of divided target images to the identifying model. In other words, the identifying unit 33 inputs all the divided target images including a background B and the like other than the product S to the identifying model. In accordance with the input of divided target image to the neural network NW2 of the identifying model, the identifying unit 33 acquires an identification result including an output value output from the neural network NW2 for each divided target image.

The identifying unit 33 acquires a product likelihood indicating the likelihood of being a product and a non-product likelihood indicating the likelihood of being a non-product in the process result acquired by performing the process using the identifying model. As a process result, for example, output values such as 1:(0.02; 0.20, 0.31, 0.89, . . . ), 2:(0.89; 0.12, 0.04, 0.23, . . . ), and the like can be acquired for divided images. A process result indicates (a non-product likelihood; a product likelihood). In other words, in a process result of a divided image "1" described above, a non-product likelihood is "0.02", and a product likelihood is "0.20, 0.31, 0.89, . . . ". In this case, the process result of the divided image "1" represents that the probability of being a product is high with a product likelihood of "0.89". In the process result of the divided image "2" described above, a non-product likelihood is "0.89", and a product likelihood is "0.12, 0.04, 0.23, . . . ". In this case, the process result of the divided image "2" represents that the probability of being a background is high. The identifying unit 33 extracts a product likelihood out of likelihoods of two kinds and identifies a kind of the product on the basis of the product likelihood. More specifically, first, the identifying unit 33 eliminates divided images of which non-product likelihoods are equal to or higher than a threshold (not used for identification). Next, the identifying unit 33 extracts a product likelihood having a largest value for each divided image in the process results of the remaining divided images. The identifying unit 33 identifies a kind of the product on the basis of majority decision of the product represented by the extracted product likelihoods.

In the embodiment described above, a form in which the measuring device 100 includes the control device 3 has been described as one example. However, the measuring device 100 does not need to include the control device 3. In such a case, the measuring device 2 may have the function of the control device 3. Alternatively, one device having the functions of the measuring device 2 and the control device 3 may be included.

In the embodiment described above, a form in which the control device 3 of the measuring device 100 includes the identifying unit 33, and the control device 3 identifies a kind of product has been described as one example. However, the control device 3 may not include the identifying unit 33. For example, the identifying a kind of product may be performed by the server 200. In such a case, the server 200 transmits an identification result to the control device 3.

In the embodiment described above, a form in which the measuring system 1 includes the measuring device 100 and the server 200 has been described as one example. However, the server 200 may not be included. In such a case, the measuring device 100 may include a learned model generating unit. Alternatively, the measuring device 100 may acquire a learned model generated by another apparatus (computer) and stores the learned model in a storage unit.

In the embodiment described above, the measuring system 1 including the measuring device 100 and the server 200 has been described. However, the present invention may be composed of only the server 200. In other words, the present invention may be an apparatus that generates an identifying model used for identifying a kind of a product from a product image including the product.

In the embodiment described above, a form in which the touch panel display 31 of the control device 3 is disposed on the holding part 12 of the casing 10 has been described as one example. However, the touch panel display 31 may be disposed at a position other than the holding part 12. It is preferable that the touch panel display 31 is disposed near the measuring device 2.

In the embodiment described above, a form in which the measuring device 100 includes the display device 4 has been described as one example. However, for example, in a case in which a customer operates the measuring device 100, the display device 4 may not be included.

In the embodiment described above, a form in which the measuring device 2 and the control device 3 are disposed in the casing 10 has been described as one example. However, the form of the measuring device 100 is not limited thereto. A form in which the measuring device 2 (the measurement stand 21a) and the control device 3 are disposed in separate units, a so-called separated scale form may be employed.

In the embodiment described above, an example in which a weight of a product S accommodated in the container P is measured has been described. However, the product S may be vegetable and fruit not accommodated in the container P.

What is claimed is:

1. A learned model generating method that is a method of generating an identifying model for identifying a kind of a product from a product image in which the product is included, the learned model generating method comprising: acquiring the product image and product information relating to the kind of the product; acquiring a plurality of divided images by dividing the product image into a plurality of areas and extracting one divided image in which a shown amount of the product satisfies a predetermined condition and other divided images in which shown amounts of the product do not satisfy the predetermined condition from the plurality of divided images, and generating the identifying model by performing machine learning by associating the product information with the one divided image and associating non-product information with the other divided images.

2. The learned model generating method according to claim 1, wherein a plurality of divided images satisfying the predetermined condition are extracted from among the plurality of divided images in the extracting of predetermined divided images; and wherein the identifying model is generated by performing machine learning by associating the divided images extracted in the extracting of predetermined divided images with the product information in the generating of the identifying model.

3. The learned model generating method according to claim 2, wherein divided images in which a shown amount of objects other than the product is equal to or smaller than a threshold are extracted in the extracting of predetermined divided images.

4. The learned model generating method according to claim 2, wherein a non-product likelihood indicating a likelihood of being the divided image not including the product is acquired for each of the plurality of divided images using an extraction model generated using machine learning based on images in which the product is not included, and divided images of which the non-product likelihoods are equal to or lower than a threshold are extracted in the extracting of predetermined divided images.

5. The learned model generating method according to claim 4, wherein the extraction model is generated by acquiring a non-product image in which the product is not included, acquiring a plurality of non-product divided images by dividing the non-product image into a plurality of areas, and generating the extraction model by performing machine learning on the basis of the plurality of non-product divided images.

6. The learned model generating method according to claim 5, wherein the product image is divided such that all the areas exhibit rectangular shapes and have the same dimensions for each of the plurality of divided images in the acquiring of a plurality of divided images by performing dividing, and wherein the non-product image is divided such that the areas have the same shape and the same dimensions as those of the divided image for each of the plurality of non-product divided images in the acquiring of a plurality of non-product divided images.

7. The learned model generating method according to claim 1, wherein the product image is divided such that one divided image and the other divided images overlap each other at least partially in the acquiring of a plurality of divided images by performing dividing.

8. The learned model generating method according to claim 7, wherein the areas acquired by dividing the product image is set such that other areas are moved by a predetermined amount with respect to the one area in a first direction that is an arrangement direction of pixels of the product image or a second direction that is orthogonal to the first direction in the acquiring of a plurality of divided images by performing dividing.

9. The learned model generating method according to claim 1, wherein the product image is divided such that all the areas exhibit rectangular shapes and have the same dimensions for each of the plurality of divided images in the acquiring of a plurality of divided images by performing dividing.

10. The learned model generating method according to claim 1, further comprising comparing the product image with a base image not including the product and cutting a product area, in which at least the entire product is included, smaller than the product image from the product image, wherein the plurality of divided images are acquired by dividing the product area into the plurality of areas in the acquiring of a plurality of divided images by performing dividing.

11. A learned model generating device that is a device generating an identifying model for identifying a kind of a product from a product image in which the product is included, the learned model generating device comprising: an acquisition unit acquiring the product image and product information relating to the kind of the product; a dividing unit acquiring a plurality of divided images by dividing the product image into a plurality of areas; an extraction unit extracting one divided image in which a shown amount of the product satisfies a predetermined condition and other divided images in which shown amounts of the product do not satisfy the predetermined condition from among the plurality of divided images; and a generation unit generating the identifying model by performing machine learning by associating the product information with the one divided image and associating non-product information with the other divided images.

12. A product identifying method of identifying a kind of a product from a target image in which the product is included using an identifying model generated using the learned model generating method according to claim 1, the product identifying method comprising: acquiring a plurality of divided target images by dividing the target image into a plurality of areas; acquiring a plurality of divided target images satisfying a predetermined condition relating to a shown amount of the product from among the plurality of divided target images; and acquiring a process result acquired by performing a process using the identifying model for the plurality of divided target images acquired in the acquiring of a plurality of divided target images satisfying a predetermined condition and identifying a kind of the product on the basis of the process result.

13. The product identifying method according to claim 12, wherein divided target images in which the shown amount of objects other than the product is equal to or smaller than a threshold are acquired in the acquiring of a plurality of divided target images satisfying a predetermined condition.

14. The product identifying method according to claim 12, wherein a non-product likelihood indicating a likelihood of being the divided target image not including the product is acquired for each of the plurality of divided target images using an acquisition model generated using machine learning based on an image in which the product is not included, and divided target images of which non-product likelihoods are equal to or smaller than a threshold are acquired in the acquiring of a plurality of divided target images satisfying a predetermined condition.

15. The product identifying method according to claim 12, wherein the target image is divided such that the areas exhibit rectangular shapes and have the same dimensions for each of the plurality of divided target images in the acquiring of a plurality of divided target images by dividing the target image.

16. A product identifying method of identifying a kind of a product from a target image in which the product is included using an identifying model generated using the learned model generating method according to claim 1, the product identifying method comprising: acquiring a plurality of divided target images by dividing the target image into a plurality of areas; and acquiring a product likelihood indicating a likelihood of being the product and a non-product likelihood indicating a likelihood of being an object other than the product in a process result acquired by performing a process using the identifying model for the plurality of divided target images acquired in the acquiring of a plurality of divided target images and identifying a kind of the product on the basis of the product likelihood.

17. The product identifying method according to claim 12, wherein a plurality of process results are acquired by performing the process using the identifying model for each of the plurality of divided target images, and the kind of the product is identified on the basis of the plurality of process results in the acquiring of a product likelihood and a non-product likelihood and the identifying of a kind of the product.

18. The product identifying method according to claim 12, wherein weighting is performed for the process result on the basis of a magnitude of a degree of a product likelihood indicating a likelihood of the product being one kind, and the kind of the product is identified on the basis of a majority decision of weightings assigned to the process result in the acquiring of a product likelihood and a non-product likelihood and the identifying of a kind of the product.

19. The product identifying method according to claim 12, wherein, in a case in which a plurality of products are included in the target image, a kind of each of the plurality of products is identified on the basis of the process result for each area including each of the plurality of products in the acquiring of a product likelihood and a non-product likelihood and the identifying of a kind of the product.

20. A product identifying device that identifies a kind of a product from a target image in which the product is included using an identifying model generated using the learned model generating method according to claim 1, the product identifying device comprising: a first acquisition unit acquiring a plurality of divided target images by dividing the target image into a plurality of areas; a second acquisition unit acquiring a plurality of divided target images satisfying a predetermined condition relating to a shown amount of the product from among the plurality of divided target images; and an identifying unit acquiring a process result acquired by performing a process using the identifying model for the plurality of divided target images acquired by the second acquisition unit and identifying the kind of the product on the basis of the process result.

21. A product identifying system comprising: a generation device generating an identifying model used for identifying a kind of a product from a product image in which the product is included; and an identifying device identifying the kind of the product from a target image in which the product is included, wherein the generation device includes: an acquisition unit acquiring the product image and product information relating to the kind of the product; a dividing unit acquiring a plurality of divided images by dividing the product image into a plurality of areas; an extraction unit extracting a plurality of first divided images in which shown amounts of the products satisfy a predetermined condition and a plurality of second divided images in which shown amounts of the product do not satisfy the predetermined condition from among the plurality of divided images; and a generation unit generating the identifying model by performing machine learning by associating the plurality of first divided images extracted by the extraction unit with the product information and associating the plurality of second divided images extracted by the extraction unit with non-product information, and wherein the identifying device includes: a first acquisition unit acquiring a plurality of second divided images by dividing the target image into a plurality of areas; a second acquisition unit acquiring a plurality of first divided images satisfying a predetermined condition relating to a shown amount of the product from among the plurality of divided images; and an identifying unit acquiring a process result acquired by performing a process using the identifying model for the plurality of first divided images acquired by the second acquisition unit and identifying the kind of the product on the basis of the process result.

22. A measuring device that identifies a kind of a product from a target image in which the product is included using an identifying model generated using the learned model generating method according to claim 1 and calculates a price of the product, the measuring device comprising: a measuring unit measuring a weight of the product; an imaging unit imaging the product; an identifying unit acquiring a process result acquired by performing a process using the identifying model for the target image that is imaged by the imaging unit and identifying the kind of the product on the basis of the process result; and a calculation unit calculating a price of the product on the basis of the weight of the product measured by the measuring unit and the kind of the product identified by the identifying unit.

* * * * *